(12) United States Patent
Che et al.

(10) Patent No.: US 7,811,675 B2
(45) Date of Patent: Oct. 12, 2010

(54) ELECTROLUMINESCENT METALLO-SUPRAMOLECULES WITH TERPYRIDINE-BASED GROUPS

(75) Inventors: Chi-Ming Che, Hong Kong (CN); Sze-Chit Yu, Aberdeen (HK)

(73) Assignee: The University of Hong Kong, Hong Kong (CN)

( * ) Notice: Subject to any disclaimer, the term of this patent is extended or adjusted under 35 U.S.C. 154(b) by 0 days.

(21) Appl. No.: 10/290,120
(22) Filed: Nov. 6, 2002

(65) Prior Publication Data
US 2004/0086744 A1    May 6, 2004

(51) Int. Cl.
*H01L 51/54* (2006.01)
*C09K 11/06* (2006.01)
(52) U.S. Cl. .................. 428/690; 428/917; 313/504; 313/506; 252/301.16; 252/301.35; 257/40
(58) Field of Classification Search ............... 428/690, 428/917; 313/504, 506; 257/40; 252/301.35, 252/301.16
See application file for complete search history.

(56) References Cited

U.S. PATENT DOCUMENTS 5,004,560 A * 4/1991 Braunling et al. .......... 526/258

(Continued)

FOREIGN PATENT DOCUMENTS

WO      WO 01/62822 A1     8/2001

OTHER PUBLICATIONS

Alcock, Nathaniel et al., J. Chem. Soc., Dalton Trans., (2000), pp. 1447-1461.*

(Continued)

*Primary Examiner*—Dawn Garrett
(74) *Attorney, Agent, or Firm*—Robert D. Katz; Cooper & Dunham LLP

(57) ABSTRACT

Highly fluorescent metallo-supramolecules based on terpyridine-based monomers and transition metals have been obtained. These robust supramolecules provide high quantum yields with emissions from violet to blue, green or yellow color. They have emerged as promising emitters for polymeric light-emitting diodes (PLEDs) due to desirable properties such as high luminance, high purity, low cost, and good thermal stabilities. The supramolecule has molecular structure represented by the formula I

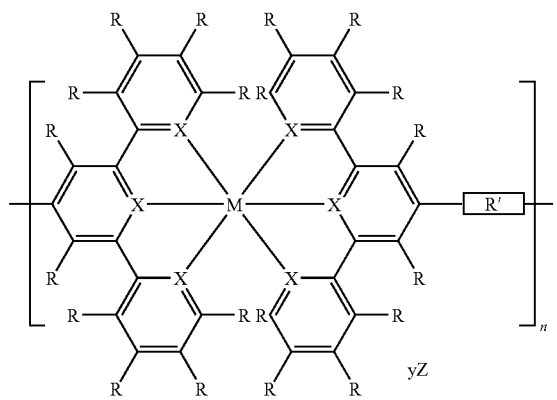

wherein M represents Group IB, IIB VIIA, VIIIA or lanthanide metals; R is independently in each occurrence and is selected from the group consisting of hydrogen, halogen, alkyl, substituted alkyl, aryl, substituted aryl, or recognized donor and acceptor groups; X is independently in each occurrence and is nitrogen or carbon atom; R is selected from alkoxy, aryloxy, heteroaryloxy, alkyl, aryl, heteroaryl, alkyl ketone, aryl ketone, heteroaryl ketone, alkylester, arylester, heteroarylester, alkylamide, arylamide, heteroarylamide, alkylthio, arylthio, fluoroalkyl, fluoroaryl, amine, imide, carboxylate, sulfonyl, alkyleneoxy, polyalkyleneoxy, or combination thereof; n is an integer of 1 to 100,000; Z is a counter ion and is selected from the group of acetate, acetylacetonate, cyclohexanebutyrate, ethylhexanoate, halide, hexafluorophosphate, hexafluoroacetylacetonate, nitrate, perchlorate, phosphate, sulfate, tetrafluoroborate or fluoromethanesulfonate; y is an integer of 0 to 4.

14 Claims, 16 Drawing Sheets

Schematic diagram of PLED in the present invention

U.S. PATENT DOCUMENTS

| | | | | |
|---|---|---|---|---|
| 5,364,726 | A | * | 11/1994 | Morrison et al. ............ 430/115 |
| 5,401,827 | A | | 3/1995 | Holmes et al. .............. 528/374 |
| 5,747,182 | A | | 5/1998 | Friend et al. ................ 428/690 |
| 6,169,163 | B1 | | 1/2001 | Woo et al. ................... 528/397 |
| 6,284,435 | B1 | | 9/2001 | Cao ............................ 430/319 |
| 6,392,339 | B1 | * | 5/2002 | Aziz et al. .................. 313/504 |
| 6,962,910 | B2 | * | 11/2005 | Brewer et al. ............... 514/188 |
| 2002/0033910 | A1 | * | 3/2002 | Ohnishi et al. ................ 349/69 |
| 2004/0215000 | A1 | * | 10/2004 | Christou ...................... 534/15 |

OTHER PUBLICATIONS

Akasaka, Tetsuo et al., Chem. Eur. J. (20002), vol. 8, No. 1, pp. 130-136.*

Wang, Xian-yong, et al., Chem. Commun., (2002), pp. 2344-2345.*

Collin, Jean-Paul et al., J. Am. Chem. Soc., (1999), vol. 121, pp. 5009-5016.*

Haider et al., "Metallocyclodextrins as Building Blocks in Noncovalent Assemblies of Photoactive Units for the Study of Photoinduced Intercomponent Processes", Inorganic Chemistry, (2001), vol. 40, p. 3912-3921.*

Schubert et al., Macromolecular Symposia, (2001), vol. 163, p. 177-187.*

Polymeric Materials: Science and Engineering, (2002), vol. 87, p. 237-238.*

Tetrahedron Letters, vol. 42, (2001), p. 4705-4707.*

Macromol. Rapid. Commun., (2000), vol. 21, p. 1156-1161.*

"Alkoxy: Definitions from Answers.com". Answers.com. Jan. 22, 2009<http://www.answers.com/topic/alkoxy>.*

Storrier et al., J. Chem. Soc., Dalton Trans., 1996, pp. 2185-2186.*

Storrier et al., J. Chem. Soc., Dalton Trans., 1997, pp. 3011-3028.*

Halcrow et al., J. Chem. Soc., Dalton Trans., 1998, pp. 2477-2482.*

Petra Herguth et al., Article entitled: "Highly Efficient Fluorene-and Benzothiadiazole-based Conjugated Copolymers for Polymer Light-emitting Diodes", *Macromolecules* 35:pp. 6094-6100 (2002).

Samson A. Jenekhe et al., entitled: "New Conjugated Polymers with Donor-Acceptor Architectures: Synthesis and Photophysics of Carbazole-Quinoline and Phenothiazine-Quinoline Copolymers and Oligomers Exhibiting Large Intramolecular Charge Transfer", *Macromolecules* 34:pp. 7515-7324 (2001).

Brenda Whittle et al., entitled: "Crystal Structures of a series of $Co^{II}$, $Cu^{II}$ and $Zn^{II}$ complexes of 4'-(3,4-dihydroxyphenyl)-2,2':6',2"-terpyridine and 4'-(3,4-dimethoxyphenyl)-2,2':6',2"-terpyridine", *Polyhedron*, vol. 17, No. 2-3 pp. 373-379 (1998).

Xuejun Zhang et al., entitled: "Electroluminescence of Multicomponent Conjugated Polymers, 2. Photophysics and Enhancement of Electroluminescence from Blends of Polyquinolines". *Macromolecules* 35: pp. 382-393 (2002).

Marcel Heller et al., entitled: "Polystyrene with Pendant Mixed Functional Ruthenium (II)-Terpyridine Complexes", *Macromol. Rapid Commun.* 23:pp. 411-415 (2002).

Marcel Heller et al., entitled: "Optically Active Supramolecular Poly(L-lactide)s End-Capped with Terpyridine", *Macromol. Rapid Commun.* 22:pp. 1358-1363 (2001).

Mutsumi Kimura et al., entitled: "Synthesis and Characterization of a Ligand-Substituted Poly(amidoamine) Dendrimer with External Terpyridine Units and its Iron(II) Complexes", *Macromol. Rapid. Commun.* 20:pp. 98-102 (1999).

Diego J. Diaz et al., entitled: "Redox Active Ordered Arrays via Metal Initiated Self-Assembly of Terpyridine Based Ligands", *J. Phys. Chem. B* 105:pp. 8746-8754 (2001).

Muhammad S. Khan et al., entitled: "Structural Characterisation of a Series of Acetylide-functionalised Oligopyridines and the Synthesis, Characterisation and Optical Spectroscopy of Platinum Di-ynes and Poly-ynes Containing Oligopyridyl Linker Groups in the Backbone", *J. Chem. Soc. Dalton Trans.* pp. 1358-1368 (2002).

Wai Yue Ng et al., entitled: "Electronic and Light-Emitting Properties of Some Polyimides Based on *Bis*(2.2':6',2"-terpyridine) Ruthenium(II) Complex", *Chem. Mater.* 11:pp. 1165-1170 (1999).

Rainer Dobrawa et al., entitled: "Photoluminescent Supramolecular Polymers: Metal-ion Directed Polymerization of Terpyridine-functionalized Perylene Bisimide Dyes", *Chem Commun.* pp. 1878-1879 (2002).

Edwin C. Constable, entitled: "Metallodendrimers: Metal Ions as Supramolecular Glue", *Chem. Commun.* pp. 1073-1080 (1997).

Wai Kin Chan et al., entitled: "Photoconductivity and Charge Transporting Properties of Metal-Containing Poly(*p*-phenylenevinylene)s", *Appl. Phys. Lett.* 71: pp. 2919-2921 (1997).

Arno Kraft et al., entitled: "Electroluminescent Conjugated Polymers-Seeing Polymers in a New Light", *Angew. Chem. Int. Ed.* 37:402-428 (1998).

Martin Grell et al., entitled: "Polarized Luminescence From Oriented Molecular Materials", *Adv. Mater.* 11: No. 11 (1999), pp. 895-896.

Chi Tak Wong et al., entitlted:"Yellow Light-Emitting Poly(phenylenevinylene) Incorporated with Pendant Ruthenium Bipyridine and Terpyridine Complexes" Adv. Mater 11: No. 6 (1999), pp. 455-459.

* cited by examiner

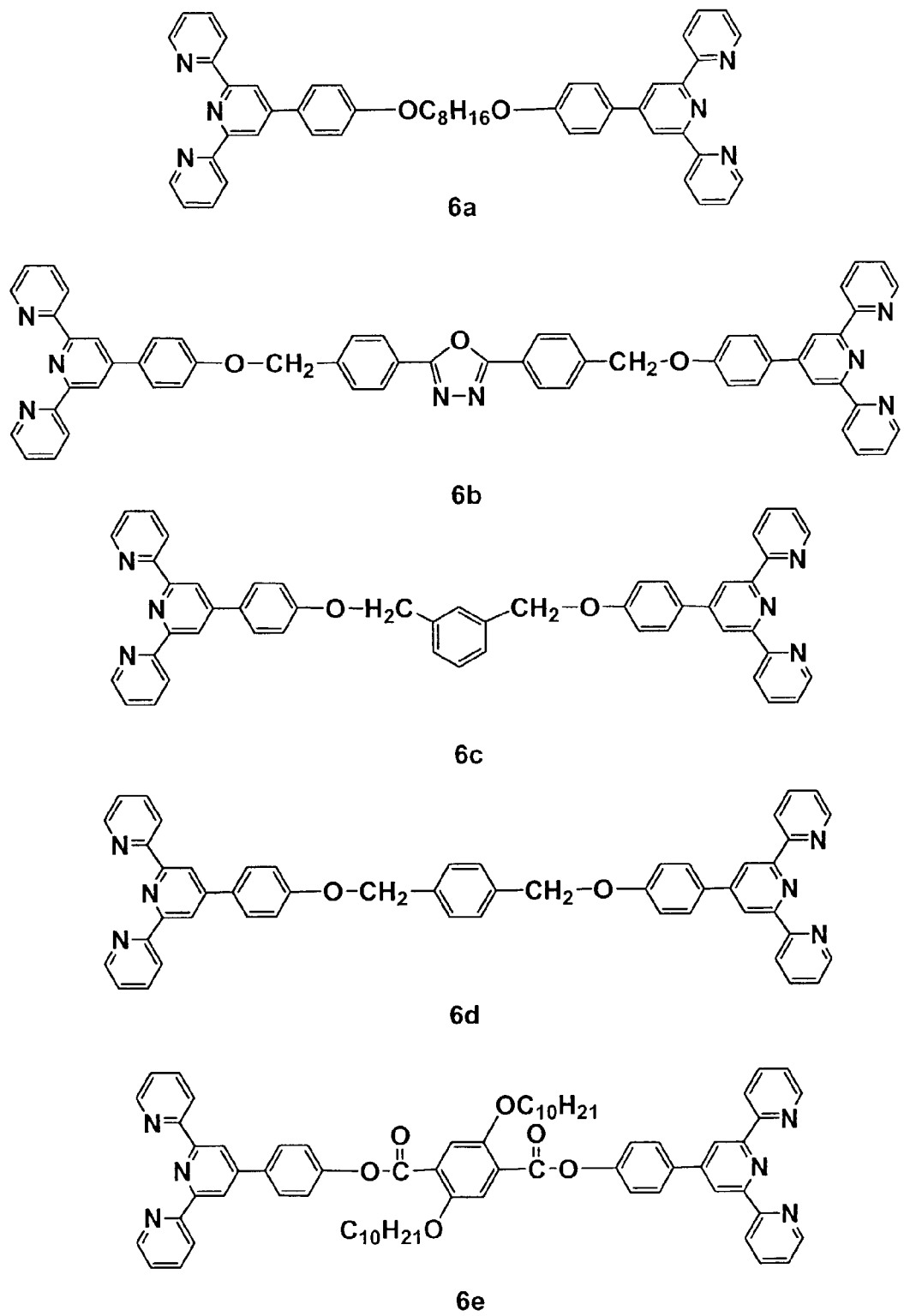
Figure 1. Structures of terpyridine-based monomers 6a - 6e

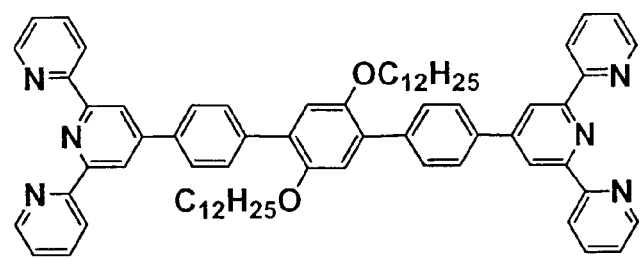
6f
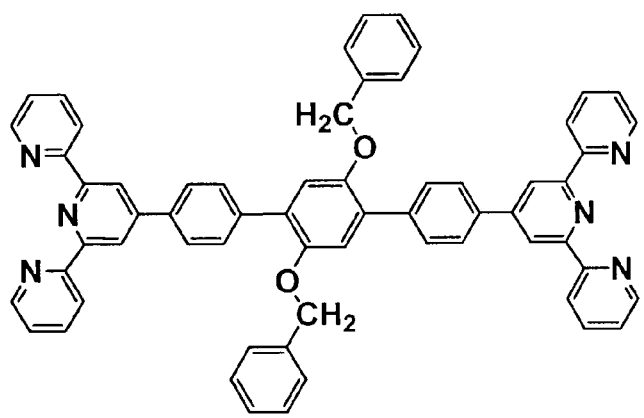
6g
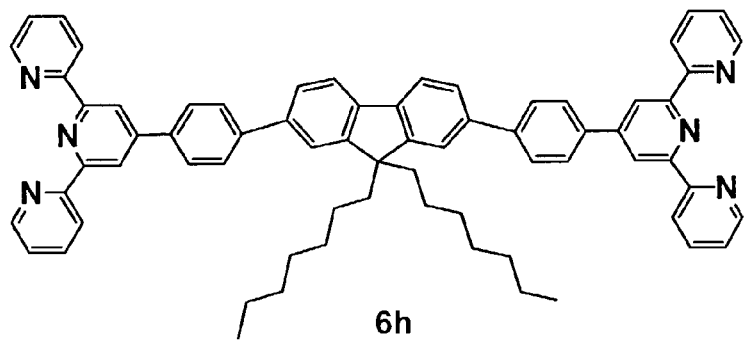
6h
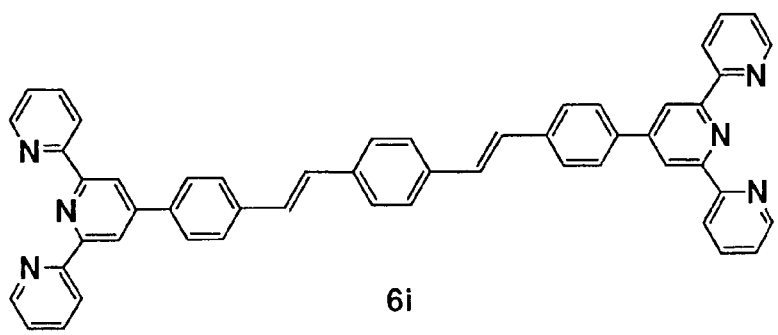
6i
Figure 2. Structures of terpyridine-based monomers 6f - 6i

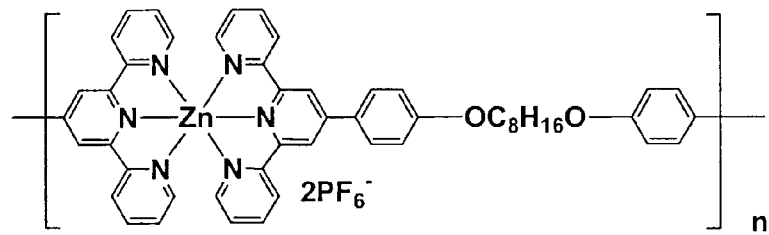
7a
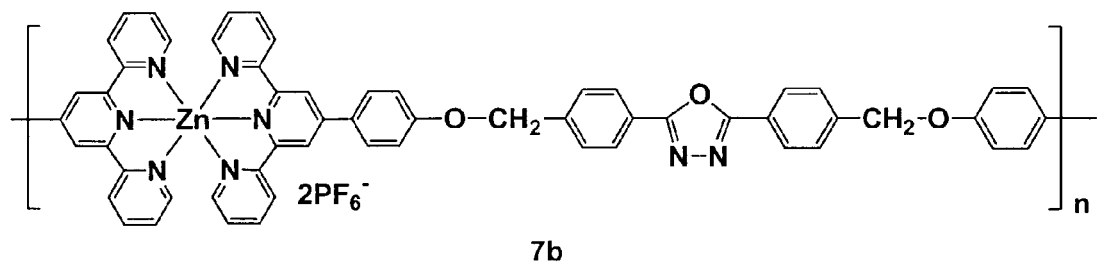
7b
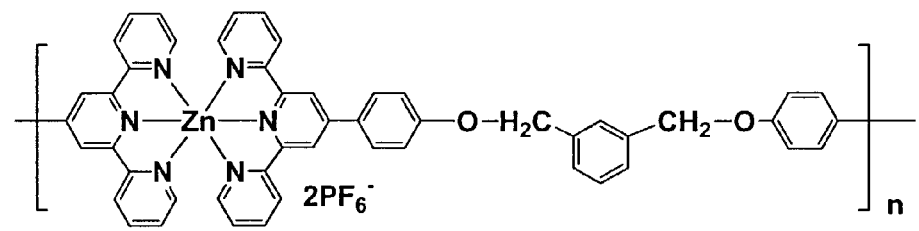
7c
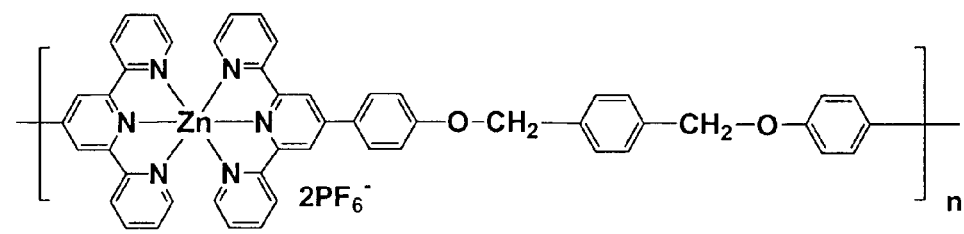
7d
Figure 3. Structures of terpyridine-based polymers 7a-7d

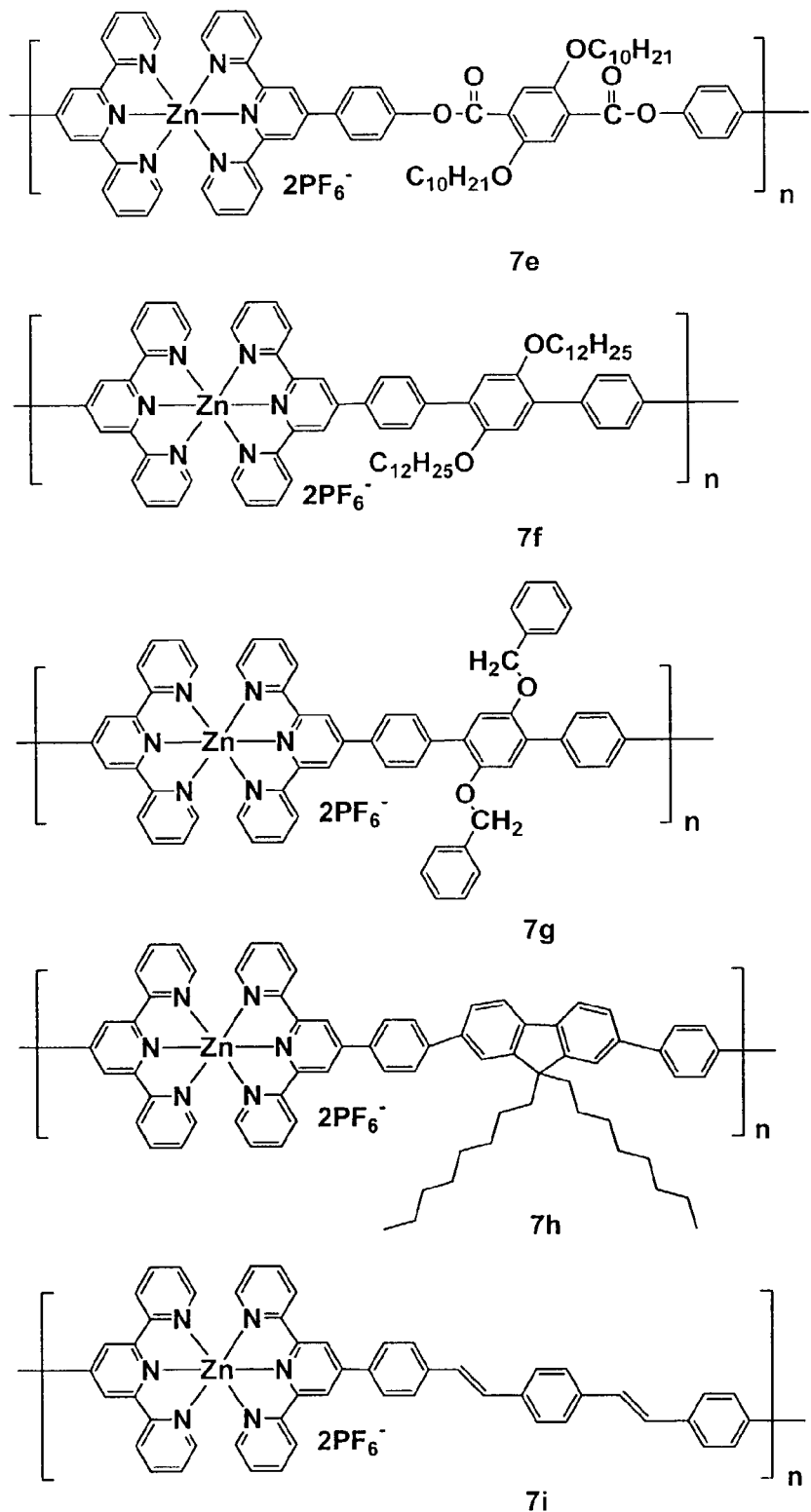
Figure 4. Structures of terpyridine-based polymers 7e - 7i

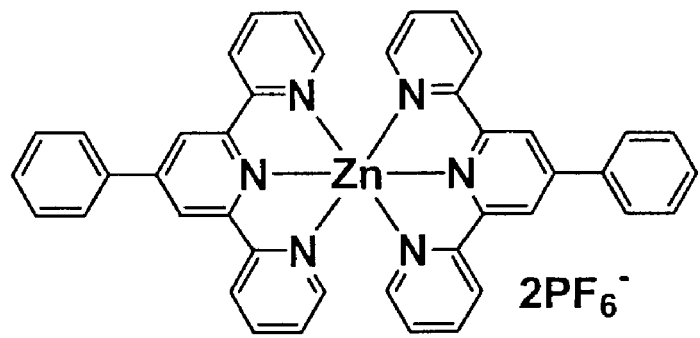
Model Compound 5a
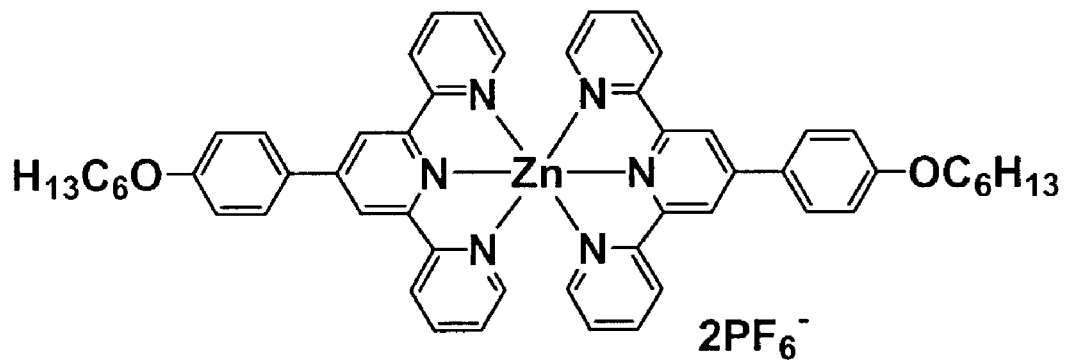
Model Compound 5b
Figure 5. Structures of model compounds 5a and 5b

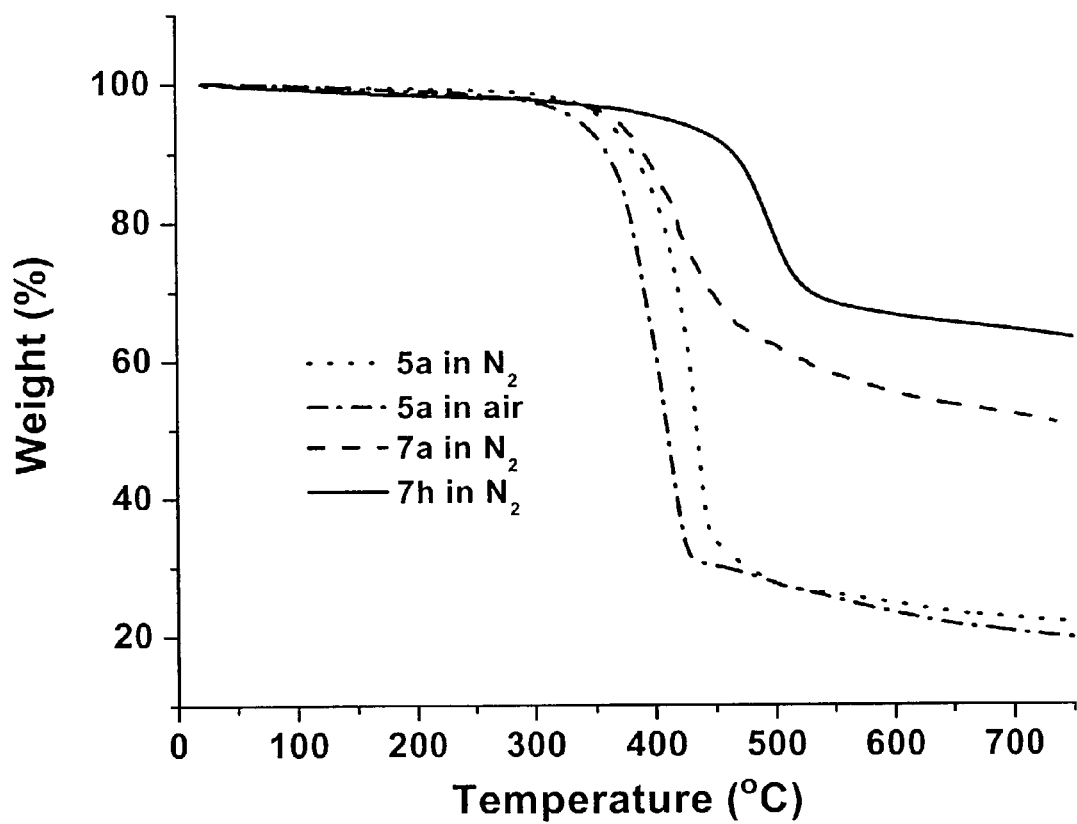
Figure 6. TGA thermograms of model compound 5a and polymers 7a and 7h

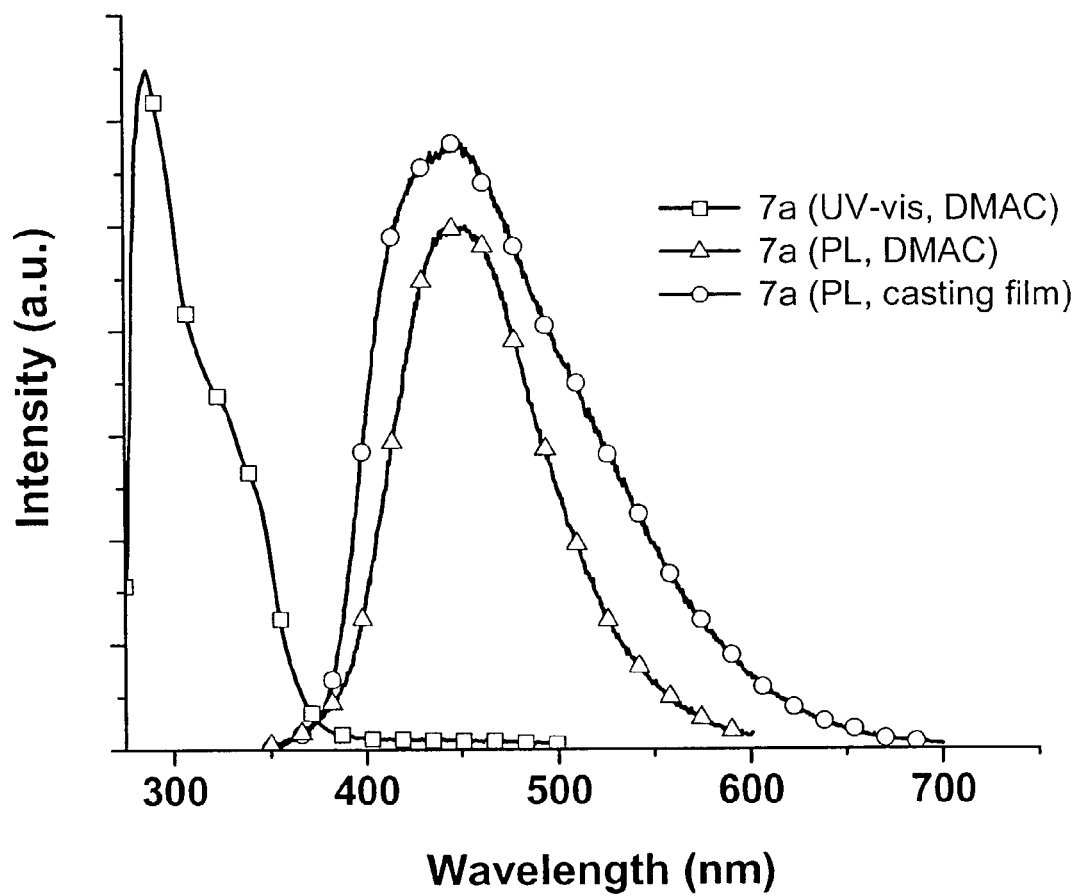
Figure 7. UV-vis and PL spectra of polymer 7a

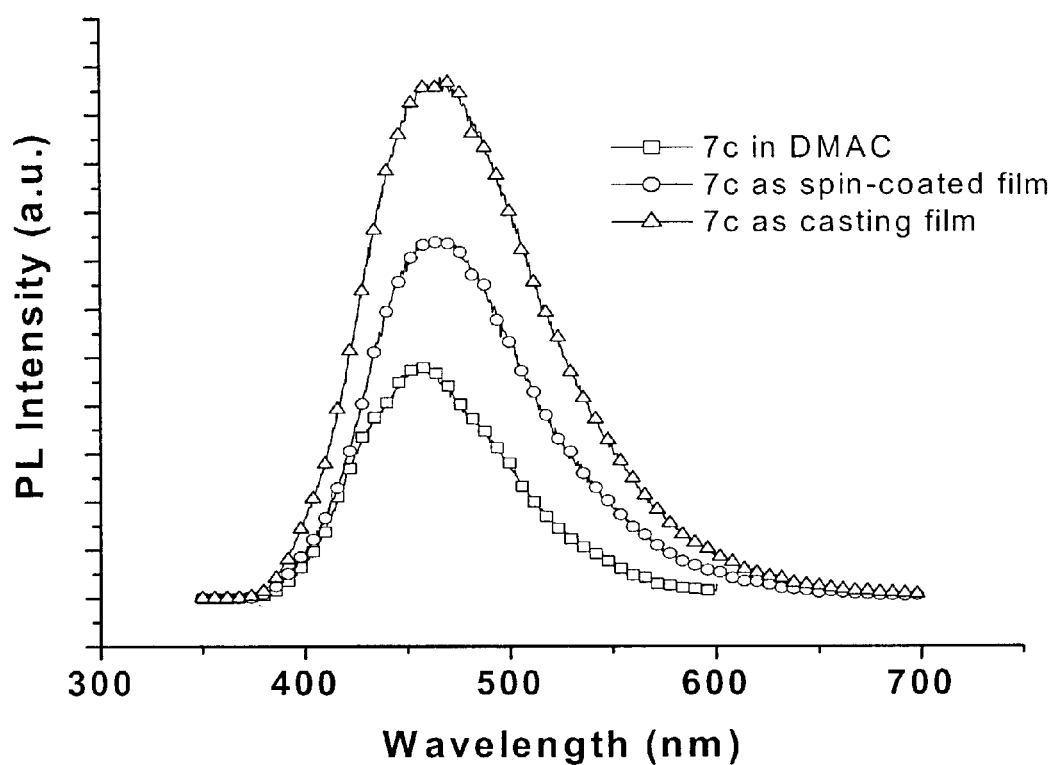
Figure 8. Emission spectra of polymer 7c in DMAC and as spin-coated and casting films

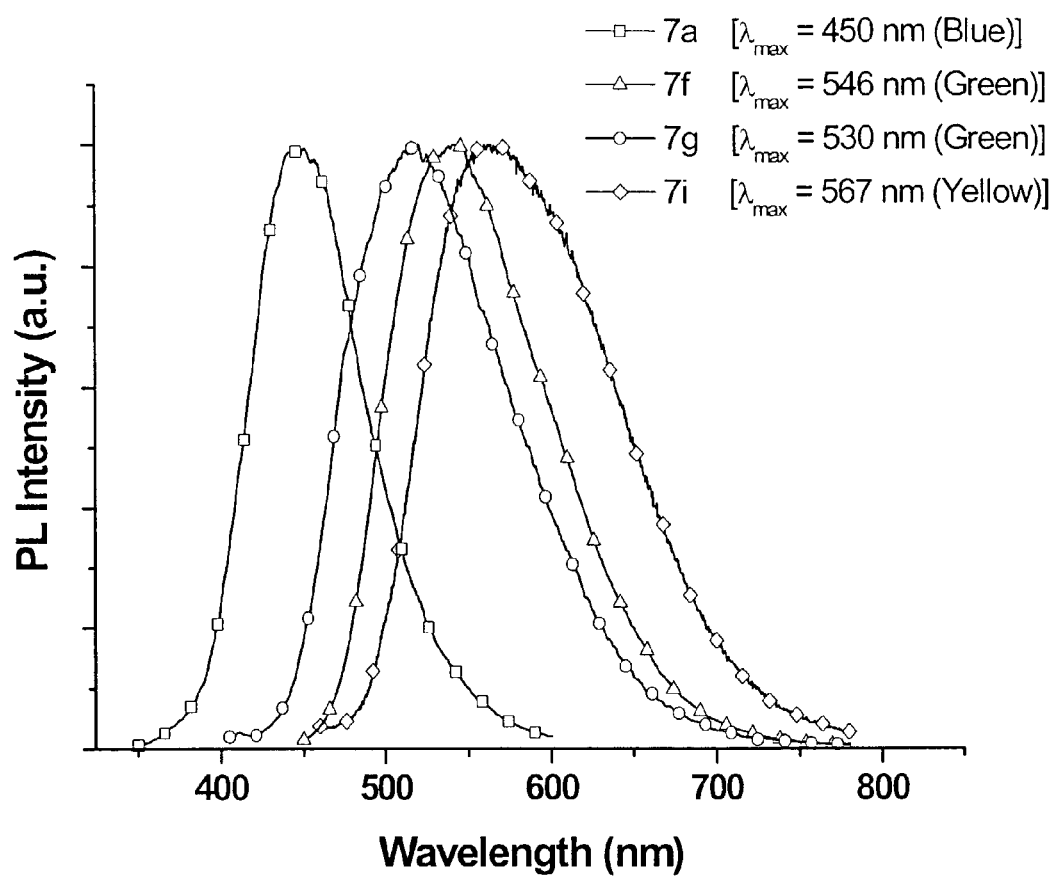
Figure 9. Emission spectra of polymers 7a, 7f, 7g, and 7i as spin-coated films

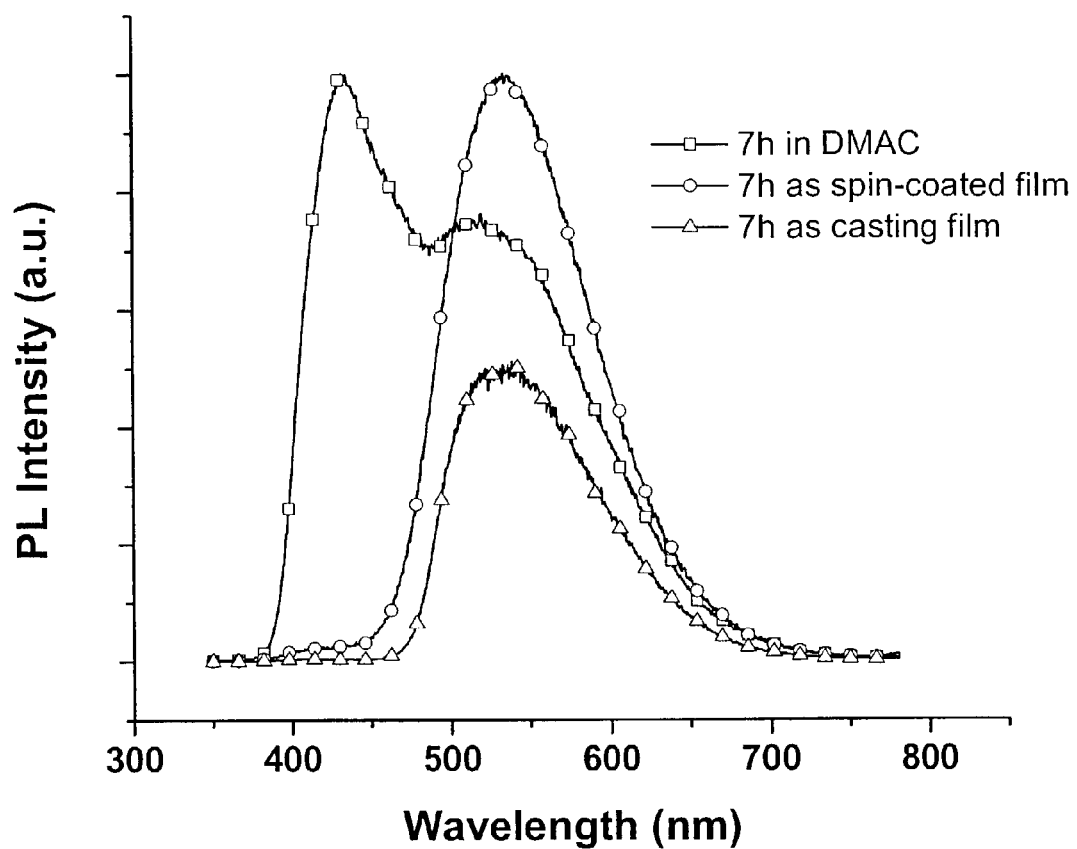
Figure 10. Emission spectra of polymer 7h in DMAC and as spin-coated and casting films

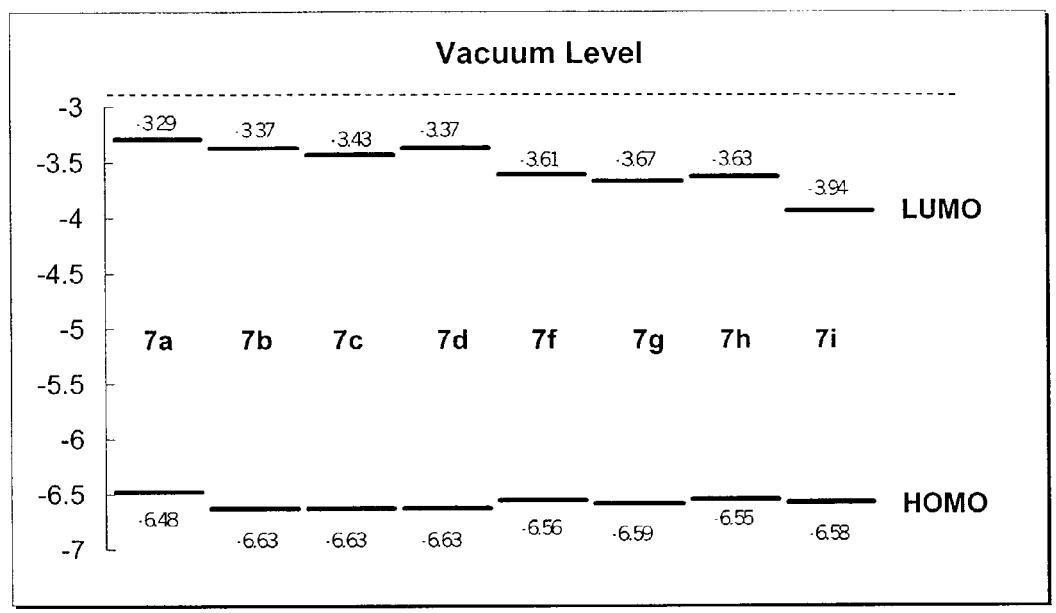
Figure 11. Schematic energy diagram for metallo-supramolecules

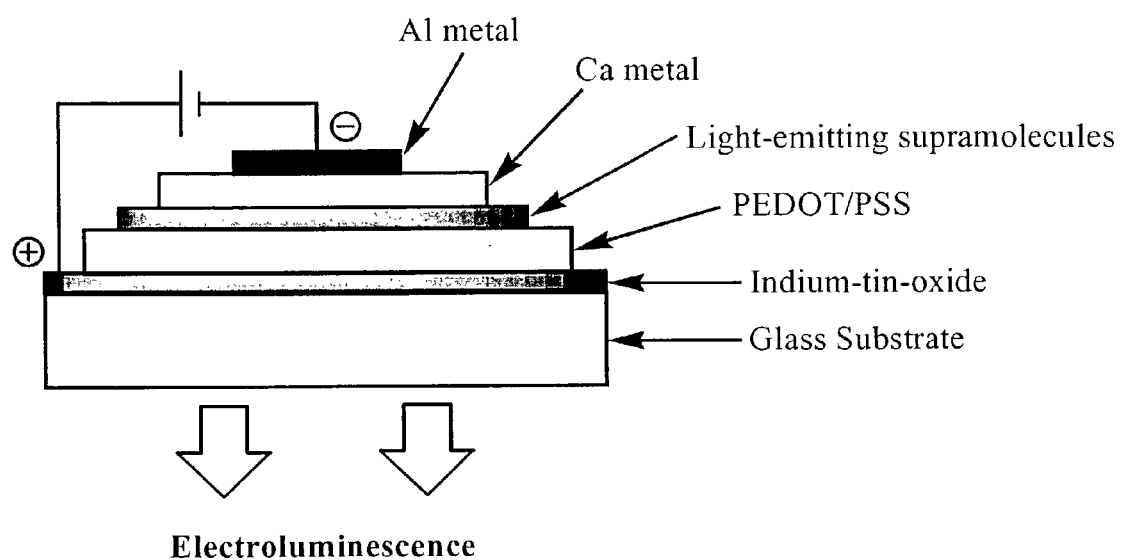
Figure 12. Schematic diagram of PLED in the present invention

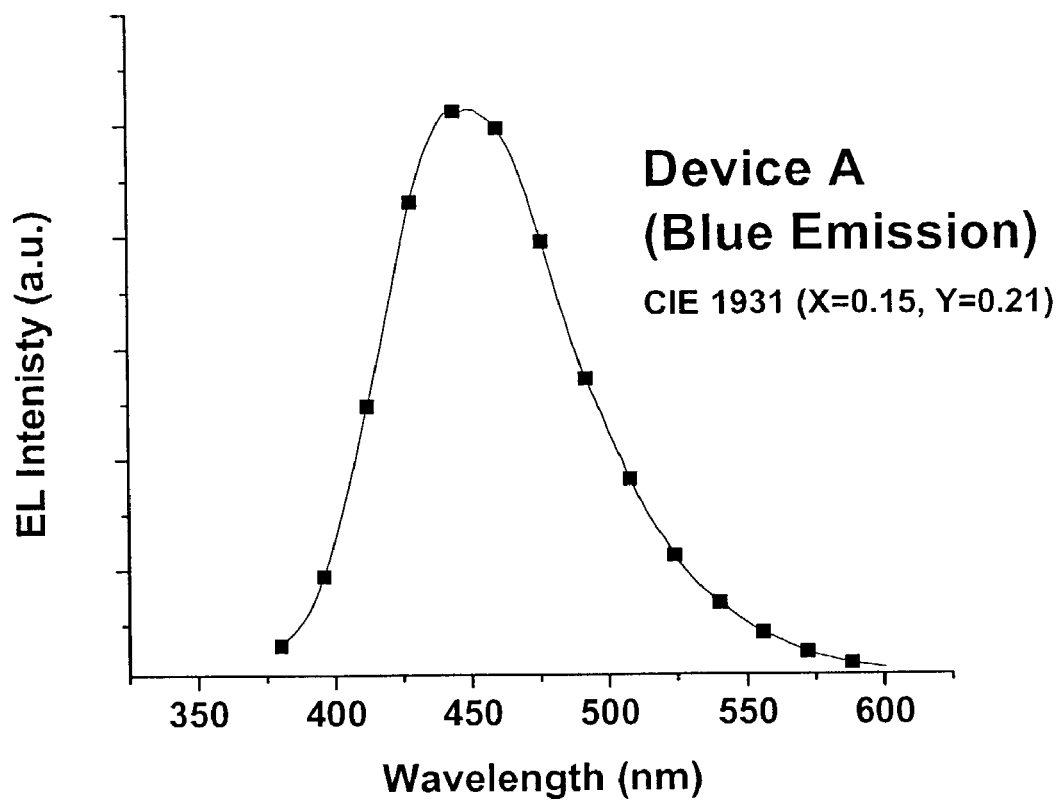
Figure 13. Electroluminescent spectrum of device A

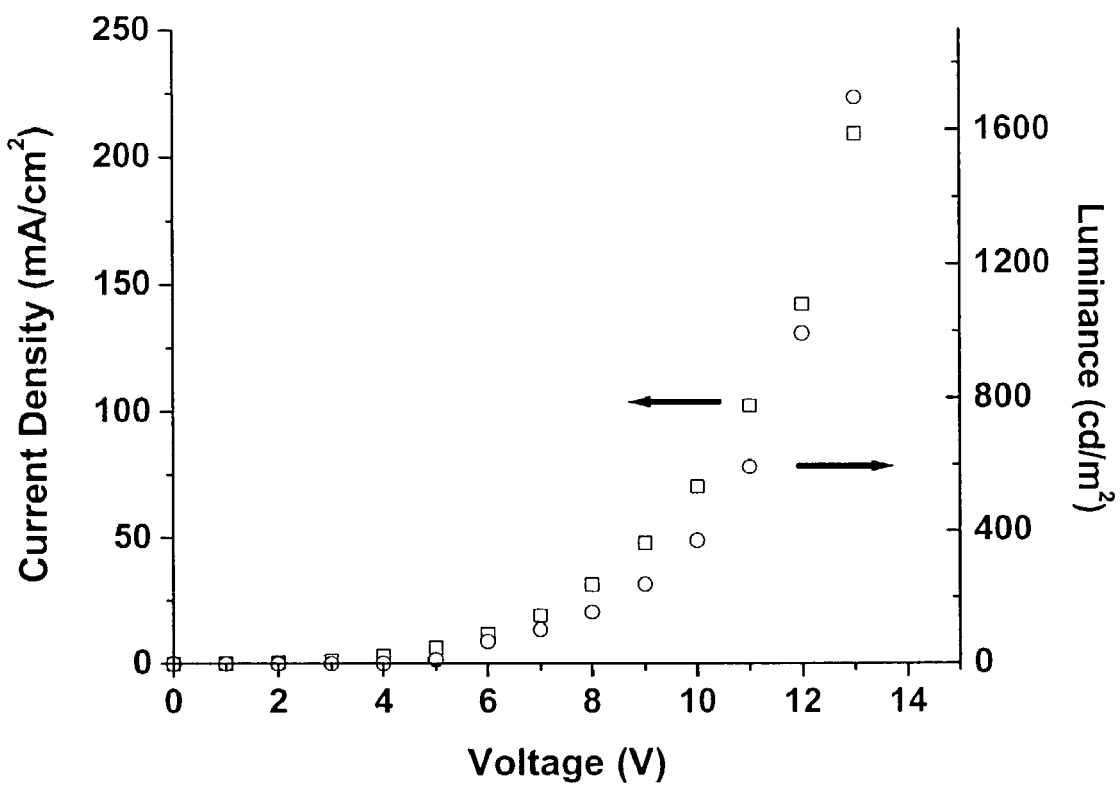
Figure 14. Current density-voltage-luminance curves of device A

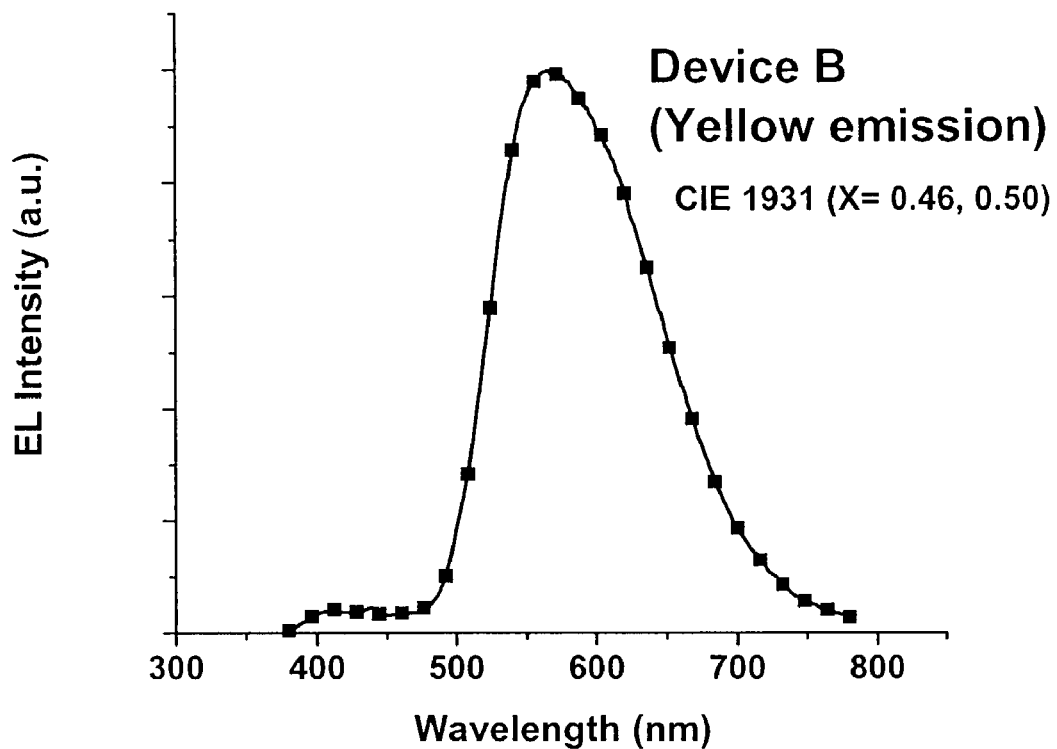
Figure 15. Electroluminescent spectrum of device B

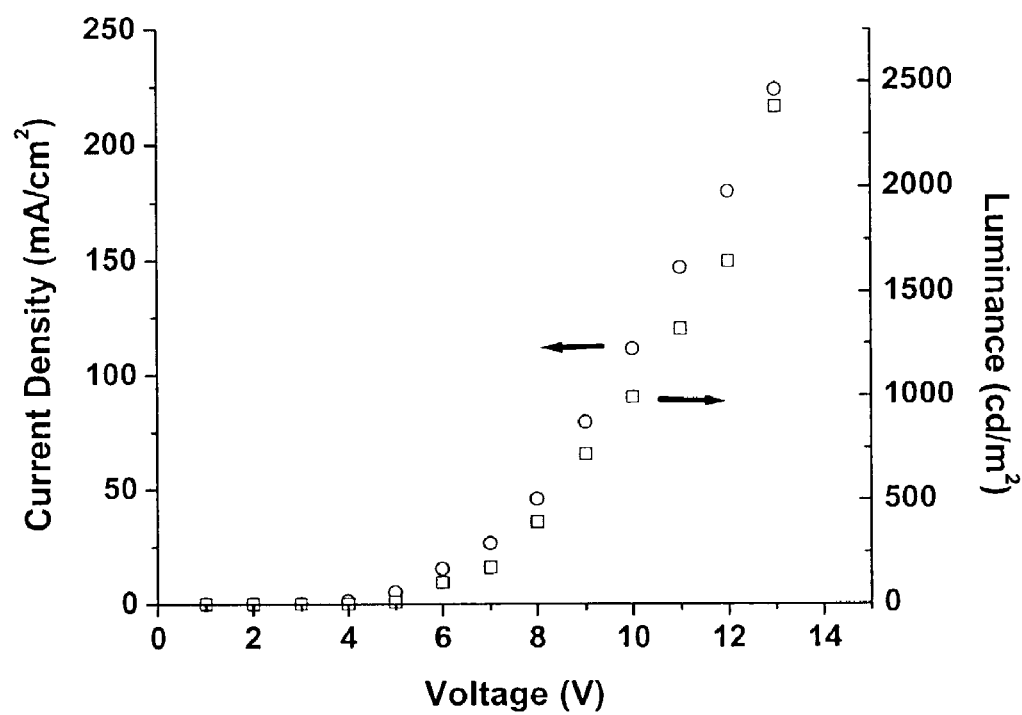
Figure 16. Current density-voltage-luminance curves of device B

ELECTROLUMINESCENT METALLO-SUPRAMOLECULES WITH TERPYRIDINE-BASED GROUPS

FIELD OF THE INVENTION

The present invention relates to highly fluorescent metallo-supramolecules, which show strong and different color emissions through variation of the moieties of the supramolecules, and which provide new sights into the design of efficient light-emitting polymers and devices for electroluminescence.

BACKGROUND

Products featuring organic and polymeric light-emitting devices (OLEDs and PLEDs) were first introduced into the market in 1999 and in 2002. Attracted by many advantages over LCD technology such as simple structure, thin-layer thickness, light-weight, wide viewing angle, low operating voltage, and possibility of producing large area display, over 100 manufacturers are engaged in the OLED and PLED development.

Organic materials including both small molecules and polymers have been employed to fabricate the devices. Developers of small molecules include Eastman Kodak Co., Idemitsu Kosan Co. Ltd., Sony Chemicals Corp., and Universal Display Corporation (UDC). Developers of polymers include Cambridge Display Technology (CDT), Dow Chemical Co., and Covion Organic Semiconductors GmbH.

Organic polymers provide considerable processing advantages over small molecules especially for the large area display. By using spin-coating or ink-jet printing method, the devices can be easily fabricated. However, blue-light PLEDs show some technical problems. These include design shortcoming, difficulties in purifying polymers, color purity problems, low efficiencies (maximum efficiency ~2.5 cd/A) and short lifetime of devices (~200 hrs at 20 mA/cm$^2$ (lifetime to half brightness)).

Among the promising materials for use as emitting layers in PLEDs, poly(phenylene vinylene) (PPV) (U.S. Pat. No. 5,747,182) and PPV derivatives such as poly(2-methoxy-5-(2'-ethylhexyloxy-1,4-phenylenevinylene) (MEH-PPV) (U.S. Pat. No. 5,401,827; U.S. Pat. No. 6,284,435) have been disclosed. Other suitable materials include poly(p-phenylene) (PPP) and related derivatives (*Angew. Chem., Int. Ed.*, 37, 402, (1998); *Adv. Mater.*, 11, 895, (1999)), polythiophene and related derivatives (*Macromolecules*, 28, 7525, (1995)), polyquinoline and related derivatives (*Macromolecules*, 35, 382, (2002); *Macromolecules*, 34, 7315, (2001)), and polyfluorene (PFO) and related derivatives (WO 01/62822 A1; U.S. Pat. No. 6,169,163; *Macromolecules*, 35, 6094, (2002)). Generally, PPV-based materials demonstrate high PL and EL efficiencies, and color turning properties. However, long-term stabilities of their EL devices are obstructed due to the photooxidative degradation. Poly(p-phenylene)s are relatively insoluble and infusible. Polythiophene and related derivates have been shown to turn the electroluminescence from blue to near-infrared but generally have low quantum efficiencies. Polyfluorenes have liquid crystalline properties that lead to rapid degradation of device performance.

It is therefore desirable to develop a robust polymeric system which can provides new sights into the design of effective light-emitting polymers, and which can be use as a high performance emissive or host materials in electroluminescence devices.

2,2':6',2''-terpyridine (terpy) has received considerable attention as strong chelating agent to metal ions in recent years. In particular with transition metals, these metal-terpy polymers have been of great interest regarding their redox behaviors and photophysical properties.

Rehahn et al. reported rod-like ruthenium (II) coordination polymer via the reaction between ruthenium (III) trichloride and terpyridine-based monomer. The intrinsic viscosity of the high-molecular-weight polymer is of order of 300 mLg$^{-1}$. Poly(p-phenylenevinylene) and polyimides which contain bis(2,2:6',2''-terpyridine) ruthenium (II) complexes in their main chains and poly(phenylenevinylene) incorporated with pendent ruthenium terpyridine complexes have been synthesized and characterized by Chan and co-workers (*Appl. Phys. Lett.*, 71, 2919, (1997); *Chem. Mater.*, 11, 1165, (1999); *Adv. Mater.*, 11, 455, (1999)). Vinyl substituted 2,2':6',2''-terpyridine and bifunctional ruthenium (II)-terpyridine complex polymers were prepared (*Macromol. Rapid Commun.*, 23, 411, (2002)).

The design and synthesis of terpyridine-based dendrimers has been another attractive field. Poly(amido amine) dendrimer with external terpyridine units and its iron (II) complexes have been reported (*Macromol. Rapid Commun.*, 20, 98, (1999)). Terpyridy-pendent poly(amido amine) and bis(terpyridine) containing ligands with Fe$^{2+}$ or Co$^{2+}$ ions were prepared by Abruña et al. (*J. Phys. Chem. B*, 105, 8746, (2001)). Some metallocentric dendrimers and metallodendrimers have been disclosed by Constable et ail (*Chem. Commun.*, 1073, (1997)).

Besides, Khan et al. reported platinum (II) poly-yne which contain terpyridyl linker groups in their main chains (*J. Chem. Soc., Dalton Trans.*, 1358, (2002)). These polymeric materials exhibit decreasing stabilities with increasing number of pyridine units in their backbones. Optically active poly(L-lactide)s, end-capped with terpyridyl group, have been prepared by Schubert et al. (*Macromol. Rapid Commun.*, 22, 1358, (2001)). Under phase-transfer conditions, iron (II)-centered poly(L-lactide)s have been synthesized. Also, Schubert and co-workers have prepared zinc and cobalt metal containing copolymers with terpyridine segments of poly(ethylene oxide) and poly(oxytetramethylene). However, only UV-vis, GPC and NMR studies were reported. Perylene bisimide-based polymer bearing bis(terpyridine) groups were performed by Würthner et al. (*Chem. Commun.*, 1878, (2002)).

In this invention, polymers based on the metal-induced and self-assembling system were prepared by simple reactions between zinc ions and terpyridine-based monomers. The octahedral coordinating geometry of the metal complex leads to the formation of stable linkages along the polymer chains. These metallo-supramolecules with well-defined architectures provide strong emissions from violet to blue, green, or yellow color with high quantum efficiencies.

SUMMARY OF THE INVENTION

The main objective of this invention is to prepare a metallo-supramolecule system and the use thereof in, for example, electroluminescent (EL) devices.

In one embodiment, the present invention is related to a molecule which acts as a tridentate ligand and forms stable complex by chelating a broad variety of transition metals.

In one embodiment, the present invention is directed to a polymer composition comprising repeat units selected from the group of terpyridine-based moieties, and to processes for synthesis and using in, for example, polymeric light-emitting diodes (PLEDs).

In one embodiment, the metallo-supramolecules are composed of terpyridine-based monomers and transition metals.

In according with the present invention, a new class of metallo-supramolecule is prepared. The preferred embodiment of the supramolecule herein is:

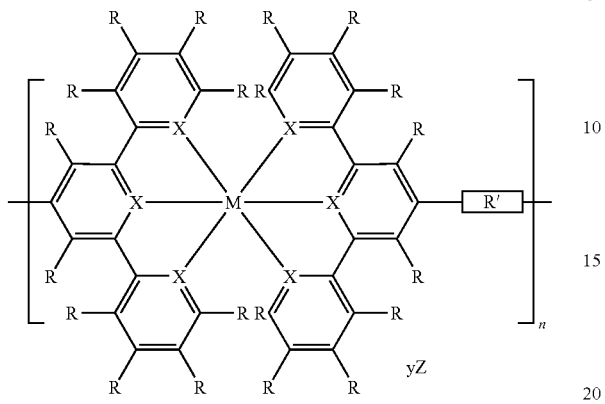

wherein M represents Group IB, IIB VIIA, VIIIA or lanthanide metals; R is independently in each occurrence and is selected from the group consisting of hydrogen, halogen, alkyl, substituted alkyl, aryl, substituted aryl, or recognized donor and acceptor groups; X is independently in each occurrence and is nitrogen or carbon atom; R' is selected from alkoxy, aryloxy, heteroaryloxy, alkyl, aryl, heteroaryl, alkyl ketone, aryl ketone, heteroaryl ketone, alkylester, arylester, heteroarylester, alkylamide, arylamide, heteroarylamide, alkylthio, arylthio, fluoroalkyl, fluoroaryl, amine, imide, carboxylate, sulfonyl, alkyleneoxy, polyalkyleneoxy, or combination thereof; n is an integer of 1 to 100,000; Z is a counter ion and is selected from the group of acetate, acetylacetonate, cyclohexanebutyrate, ethylhexanoate, halide, hexafluorophosphate, hexafluoroacetylacetonate, nitrate, perchlorate, phosphate, sulfate, tetrafluoroborate or fluoromethanesulfonate; y is an integer of 0 to 4

More particularly, the present invention, in embodiments, the supramolecules can be easily prepared by reactions between the zinc ions and the terpyridine-based monomers in N-methylpyrrolidinone (NMP).

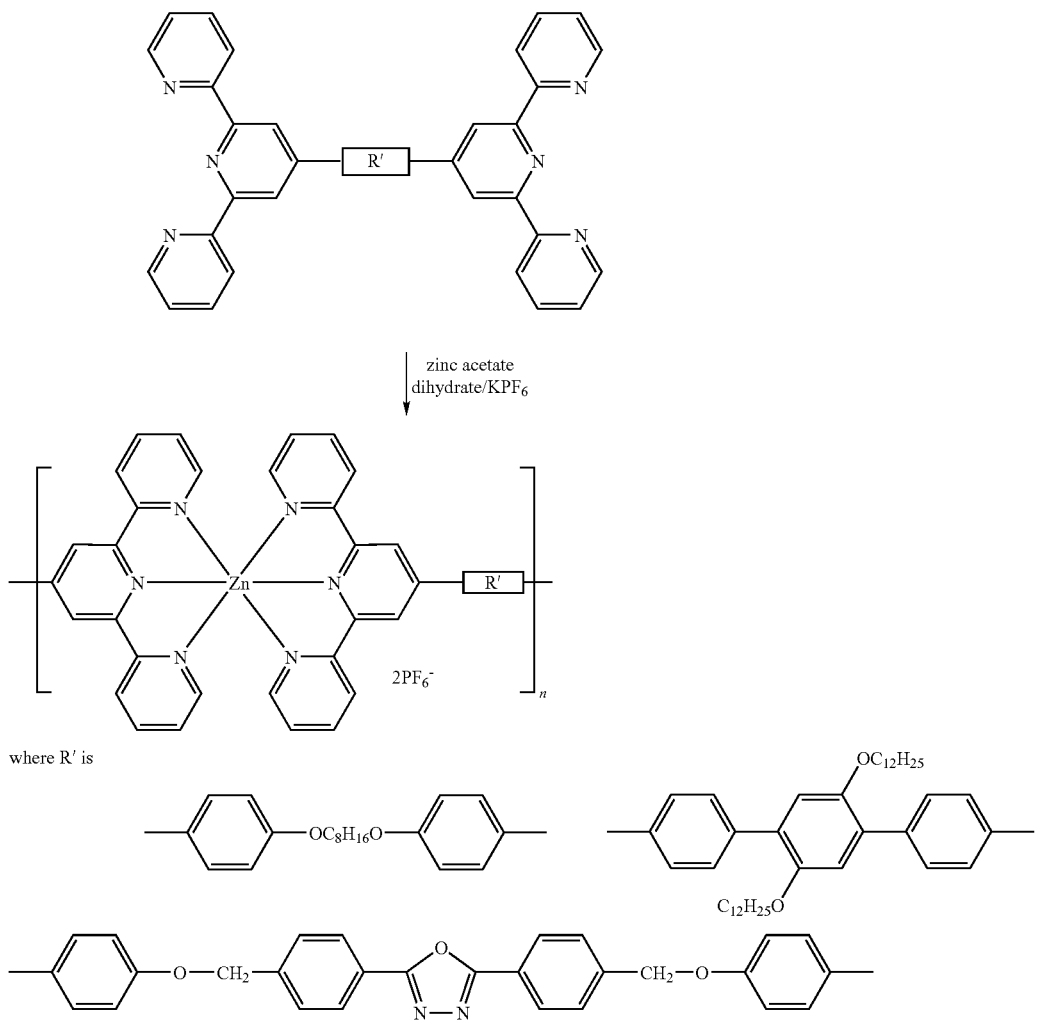

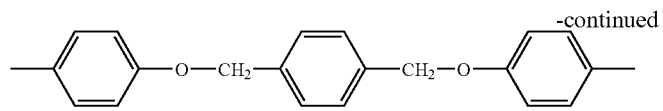

-continued

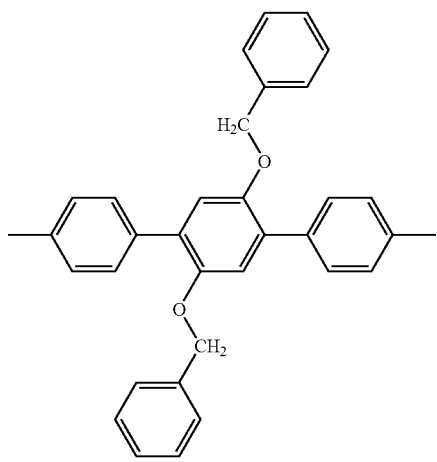

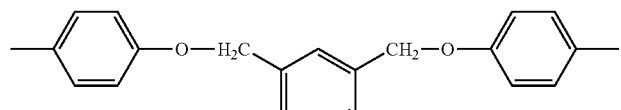

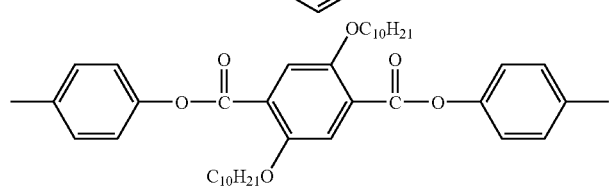

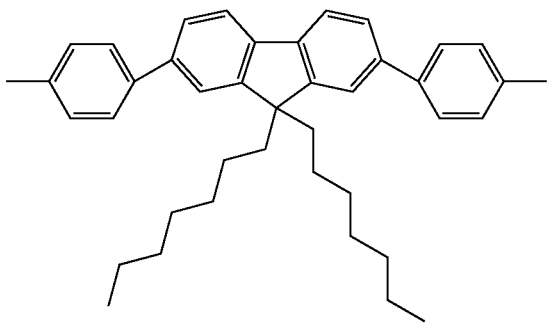

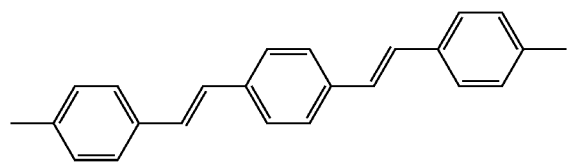

In another embodiment, each repeating unit of the supramolecules disposes in well geometrically controlled linear array. In one embodiment, by altering different R' or substituents on the R' of the supramolecules, the emission wavelength ranges from violet to blue, green or yellow and is dependent on the compositions of the polymers.

Specific embodiments of present invention are to demonstrate polymeric light-emitting diodes (PLEDs) comprising:
(a) a transparent hole-injecting anode layer
(b) a transparent hole-transporting layer
(c) an active emissive layer comprising a supramolecule and
(d) an electron-injecting cathode layer wherein transparent hole-injecting anode layer is selected from the group of high work function metals or metal alloys; transparent hole-transporting layer is selected from the group of poly(aniline) (PANI) or poly(3,4-ethylenedioxythiophene)/(poly(styrenesulfonate) (PEDOT/PSS); active emissive layer is selected from the group of metallo-supramolecules which are disclosed in this invention; and electron-injecting cathode layer is selected from the group of metals with low work functions.

BRIEF DESCRIPTION OF THE FIGURES

FIG. 1. Structures of terpyridine-based monomers 6a-6e
FIG. 2. Structures of terpyridine-based monomers 6f-6i
FIG. 3. Structures of terpyridine-based polymers 7a-7d
FIG. 4. Structures of terpyridine-based polymers 7e-7i
FIG. 5. Structures of model compounds 5a and 5b
FIG. 6. TGA thermograms of model compound 5a and polymers 7a and 7h
FIG. 7. UV-vis and PL spectra of polymer 7a
FIG. 8. Emission spectra of polymer 7c in DMAC and as spin-coated and casting films
FIG. 9. Emission spectra of polymers 7a, 7f, 7g, and 7i as spin-coated films
FIG. 10. Emission spectra of polymer 7h in DMAC and as spin-coated and casting films
FIG. 11. Schematic energy diagram for metallo-supramolecules
FIG. 12. Schematic diagram of PLED in the present invention
FIG. 13. Electroluminescent spectrum of device A FIG. 14. Current density-voltage-luminance curves of device A FIG. 15. Electroluminescent spectrum of device B FIG. 16. Current density-voltage-luminance curves of device B Table 1. Physical properties of polymers 7a to 7i and model compounds 5a and 5b Table 2. Photophysical properties of polymers 7a to 7i in DMAC and as thin-films and model compounds 5a and 5b in DMAC Table 3. HOMO-LUMO energy levels and bandgaps of supramolecules and model compounds

DETAILED DESCRIPTION OF THE INVENTION

The inventions are generally related to syntheses, spectral characterization, photoluminescence, electroluminescence of the supramolecules and their applications in polymeric light-emitting devices (PLEDs). In this invention, two series of supramolecules have been designed. In one series, the spacer unit R' is based on flexible oxymethylene linkage (—OCH$_2$—) along the main chain of the supramolecules. In the second series, the spacer is based on conjugated phenylene derivatives along the rigid backbone of the supramolecules.

The examples are set forth to aid in an understanding of the inventions but are not intended to, and should not be interpreted to, limit in any way the invention as set forth in the claims which follow thereafter.

The examples given illustrate the synthetic methods of model compounds 5a and 5b, monomers 6a, 6f and 6i, and polymer 7h. Model compounds 5a and 5b were synthesized according to a modified procedure described in the literature (*Polyhedron*, 17, 373, (1998)). By simple reactions between the zinc acetate dihydrate and the terpyridine-based monomers in N-methylpyrrolidinone (NMP), zinc metal ions were employed as assembling center to form polymers 7a-7i.

EXAMPLE 1

Synthesis of model compound 5a—zinc acetate dihydrate (1 mmol) and 4'-phenyl-2,2':6',2''-terpyridine (1 mmol) were heated at 100° C. in 10 mL N-methylpyrrolidinone (NMP) under a nitrogen atmosphere for 3 h. After filtration, excess potassium hexafluorophosphate (KPF$_6$) was added into filtrate. The precipitate was washed with methanol and the solid was recrystallized with mixture of ethanol and CH$_3$CN. Yield: 86%. FABMS: m/e 685; C$_{42}$H$_{30}$N$_6$Zn requires m/e 684.1. $^1$H NMR (DMSO, δ, ppm): 9.38 (1H, s), 9.12 (4H, d, J=8.0 Hz), 8.41 (4H, d, J=7.1 Hz), 8.27 (4H, t, J=7.5 Hz), 7.94 (4H, d, J=4.2 Hz), 7.5 (6H, m), 7.48 (4H, t, J=6.1 Hz). $^{13}$C NMR (DMSO, δ, ppm): 155.1, 149.4, 147.7, 141.2, 135.7, 131.1, 129.8, 129.4, 128.1, 127.6, 123.5, 121.1.

EXAMPLE 2

Synthesis of model compound 5b—Yield: 80%. FABMS: m/e 885; C$_{54}$H$_{54}$N$_6$O$_2$Zn requires m/e 884.4. $^1$H NMR (CDCl$_3$, δ, ppm): 9.33 (4H, s), 9.14 (4H, d, J=8.0 Hz), 8.44 (4H, d, J=8.5 Hz), 8.27 (4H, t, J=7.6 Hz), 7.93 (4H, d, J=4.7 Hz), 7.48 (4H, dd, J=12.6 Hz, J=5.6 Hz), 7.29 (4H, d, J=8.7 Hz), 4.17 (4H, t, J=6.6 Hz), 1.81 (8H, m), 1.48 (4H, m), 0.92 (6H, t, J=6.8 Hz). $^{13}$C NMR (CDCl$_3$, δ, ppm): 161.9, 155.1, 149.8, 148.3, 141.7, 130.3, 128.1, 127.7, 123.9, 120.4, 115.8, 68.4, 31.5, 29.1, 25.7, 22.6, 14.4.

EXAMPLE 3

Synthesis of monomer 6a—To a suspension of KOH (2.5 mmol) in 100 mL DMSO, 4'-(4hydroxyphenyl)-2,2':6',2''-terpyridine (2.05 mmol) was added into the mixture. After stirring for 1 h at 90° C., 1,8-dibromoctane (1.0 mmol) and KI (catalytic amount) were added. The resulting mixture was stirred for 24 h. The suspension was cooled to room temperature and poured into 500 mL water. The precipitate was filtered. The obtained solid was recrystallized from mixture of ethanol and acetone. Yield: 72%. FABMS: m/e 761; C$_{50}$H$_{44}$N$_6$O$_2$ requires m/e 760.9. $^1$H NMR (CDCl$_3$, δ, ppm): 8.71 (8H, m), 8.66 (6H, d, J=8.0 Hz), 7.86 (8H, m), 7.34 (4H, dt, J=4.8 Hz, J=1.0 Hz), 7.02 (4H, d, J=8.8 Hz), 4.04 (4H, t, J=6.5 Hz), 1.83 (4H, m), 1.50 (8H, m). $^{13}$C NMR (CDCl$_3$, δ, ppm): 156.4, 155.8, 149.8, 149.1, 136.8, 130.5, 128.5, 123.7, 121.3, 118.2, 118.1, 114.9, 68.1, 29.3, 29.2, 26.3.

EXAMPLE 4

Synthesis of monomer 6b—Yield: 60%. FABMS: m/e 898; C$_{58}$H$_{40}$N$_8$O$_3$ requires m/e 897.0. $^1$H NMR (CDCl$_3$, δ, ppm): 8.72 (8H, m), 8.66 (4H, d, J=8.0 Hz), 8.19 (4H, d, J=8.3 Hz), 7.89 (8H, m), 7.65 (4H, d, J=8.2 Hz), 7.34 (4H, m), 7.13 (4H, d, J=1.9 Hz), 5.24 (4H, s). $^{13}$C NMR (CDCl$_3$, δ, ppm): 166.1, 161.1, 158.1, 157.6, 151.4, 150.8, 142.5, 138.6, 135.9, 133.2, 130.4, 129.6, 129.0, 125.5, 125.3, 123.1, 120.1, 117.0, 100.6, 71.2.

EXAMPLE 5

Synthesis of monomer 6c—Yield: 58%. FABMS: m/e 753; C$_{52}$H$_{36}$N$_6$O$_2$ requires m/e 752.9. $^1$H NMR (CDCl$_3$, δ, ppm): 8.70 (8H, m), 8.65 (4H, d, J=8.0 Hz), 7.87 (8H, m), 7.59 (1H, s), 7.46 (3H, s), 7.33 (4H, m), 7.12 (4H, d, J=8.0 Hz), 5.18 (4H, s). $^{13}$C NMR (CDCl$_3$, δ, ppm): 156.4, 155.8, 149.1, 136.8, 131.1, 129.0, 128.6, 127.1, 126.5, 123.7, 121.3, 118.3, 115.3, 69.9.

EXAMPLE 6

Synthesis of monomer 6d—Yield: 62%. FABMS: m/e 753; C$_{52}$H$_{36}$N$_6$O$_2$ requires m/e 752.9.

EXAMPLE 7

Synthesis of monomer 6e—Yield: 52%. FABMS: m/e 1094; C$_{70}$H$_{72}$N$_6$O$_6$ requires m/e 1093.4. $^1$H NMR (CDCl$_3$, δ, ppm): 8.75 (4H, s), 8.73 (4H, d, J=4.7 Hz), 8.68 (4H, d, J=8.0 Hz), 8.00 (4H, d, J=8.6 Hz), 7.88 (4H, dt, J=7.6 Hz, J=1.7 Hz), 7.62 (2H, s), 7.38 (8H, m), 1.53 (14H, m), 1.22 (24H, m). $^{13}$C NMR (CDCl$_3$, δ, ppm): 156.1, 152.4, 149.2, 136.9, 128.5, 123.8, 122.2, 121.4, 118.8, 70.1, 31.9, 29.6, 29.3, 26.0.

EXAMPLE 8

Synthesis of monomer 6f—4'-(4-bromophenyl)-2,2':6',2''-terpyridine (2.05 mmol), 2,5-didodecyloxybenzene-1,4-diboronic acid (1 mmol), and [Pd(PPh$_3$)$_4$] (1 mol-%) were refluxed for 24 h in heterogeneous system of 25 mL toluene and 25 mL aqueous 1M Na$_2$CO$_3$. After the stirring, 100 mL water was added and the resulting mixture was extracted with CHCl$_3$ (3×100 mL). The organic layers were dried with Na$_2$SO$_4$ and removed under vacuum. The solid was recrystallized from a mixture of ethanol and chloroform (9:1; v/v). Yield: 80%. FABMS: m/e 1062; C$_{72}$H$_{80}$N$_6$O$_2$ requires m/e 1061.4. $^1$H NMR (CDCl$_3$, δ, ppm): 8.83 (4H, s), 8.73 (4H, m), 8.69 (4H, d, J=8.0 Hz), 8.01 (4H, d, J=8.3 Hz), 7.90 (4H, dt, J=7.7 Hz, J=1.1 Hz), 7.79 (4H, d, J=8.6 Hz), 7.36 (4H, m), 7.09 (2H, s), 1.72 (4H, m), 1.17 (40H, m), 0.83 (6H, m). $^{13}$C NMR (CDCl$_3$, δ, ppm): 156.4, 156.0, 150.5, 150.0, 149.2, 139.3, 136.8, 130.1, 116.9, 123.8, 121.4, 118.8, 116.3, 69.9, 31.9, 29.7, 29.6, 29.4, 29.3, 26.1, 22.7, 14.1.

EXAMPLE 9

Synthesis of monomer 6g—Yield: 70%. FABMS: m/e 954; C$_{66}$H$_{44}$N$_6$O$_2$ requires m/e 953.1. $^1$H NMR (CDCl$_3$, δ, ppm): 8.83 (4H, s), 8.77 (4H, dd, J=1.7 Hz, J=0.9 Hz), 8.69 (4H, m), 8.00 (4H, d, J=8.4 Hz), 7.90 (4H, dt, J=7.7 Hz, J=1.8 Hz), 7.77 (4H, d, J=8.4 Hz), 7.35 (4H, m), 5.10 (4H, s). $^{13}$C NMR (CDCl$_3$, δ, ppm): 156.4, 156.0, 150.3, 149.2, 136.8, 130.1, 128.5, 127.8, 127.2, 127.0, 123.8, 121.4, 118.8, 117.3, 71.8.

EXAMPLE 10

Synthesis of monomer 6h—Yield: 73%. FABMS: m/e 1006; C$_{71}$H$_{68}$N$_6$ requires m/e 1005.4. $^1$H NMR (DMSO, δ, ppm): 8.83 (4H, s), 8.76 (4H, m), 8.68 (4H, m), 8.05 (4H, m), 7.90 (4H, dt, J=7.8 Hz, J=1.8 Hz), 7.83 (6H, d, J=8.2 Hz), 7.70 (4H, m), 7.38 (4H, m), 2.11 (4H, m), 1.11 (18H, m), 0.80 (8H, m). $^{13}$C NMR (DMSO, δ, ppm): 156.4, 156.1, 151.9, 149.8, 149.2, 142.4, 140.4, 139.4, 137.2, 136.9, 127.7, 127.7, 126.1, 123.8, 121.5, 121.4, 120.2, 118.7, 55.4, 40.4, 31.8, 30.0, 29.2, 23.9, 22.6, 14.0.

EXAMPLE 11

Synthesis of monomer 6i—Divinylbenzene (1 mmol), 4'-(4-bromophenyl)-2,2':6',2''-terpyridine (2 mmol), palladium (II) acetate (5 mol-%), and tri-o-tolyphosphine (0.4 equiv.) were added to a 50 mL flask under nitrogen atmosphere. Anhydrous DMF was added via a syringe and the solution was stirred until all the solid had dissolved. Tri-n-butylamine (1 mL) was added and the solution was stirred at 100° C. for 5 days. The solution was poured into methanol. The solid was recrystallized from a mixture of ethanol and chloroform (8:2; v/v). Yield: 77%. FABMS: m/e 745; C$_{52}$H$_{36}$N$_6$ requires m/e 744.9.

EXAMPLE 12

Synthesis of polymer 7h—To a monomer 6h (0.1 mmol) in 50 mL N-methylpyrrolidinone (NMP) solution, zinc acetate dihydrate (0.1 mmol) in 5 mL NMP was added in dropwise at 105° C. After stirring for 24 h under N$_2$, excess potassium hexafluorophosphate (KPF$_6$) was added into hot solution. The resulting solution was poured into methanol and solid precipitated. Purification was performed by repetitive precipitation using DMAC and methanol. The resulting polymer was dried under vacuum at 80° C. for 24 h and collected as yellow solid. Yield: 80%.

TABLE 1

Physical properties of polymers 7a to 7i and model compounds 5a and 5b

| Compound | $\eta_{INH}^A$ (DL/G) | YIELD$^B$ (%) | $T_d$ [° C.] in N$_2$$^c$ | $T_d$ [° C.] in air$^c$ |
|---|---|---|---|---|
| 5a | / | 86 | 385 | 365 |
| 5b | / | 80 | 360 | 331 |
| 7a | 0.70 | 78 | 374 | 360 |
| 7b | 0.68 | 69 | 354 | 348 |
| 7c | 0.77 | 67 | 357 | 336 |
| 7d | 0.54 | 74 | 358 | 349 |
| 7e | 0.44 | 65 | 336 | 308 |
| 7f | 1.10 | 75 | 424 | 403 |
| 7g | 0.62 | 70 | 368 | 340 |
| 7h | 1.21 | 80 | 433 | 410 |
| 7i | 0.75 | 69 | 394 | 378 |

$^A$Inherent viscosity measured in NMP at 30 ± 0.1° C. using Ubbelohde viscometer
$^B$Yield after purification
$^c$Decomposition temperature determined by TGA with heating rate at 20° C./min The physical properties of the supramolecules are summarized in table 1. The inherent viscosities of the supramolecules range from 0.48-1.21 dL/g as determined by Ubbelohde viscometer in NMP at 30±0.1° C. The thermal behavior of the supramolecules was measured by TGA and DSC. The thermograms are depicted in FIG. 6. The onset decomposition temperatures (T$_d$) of the supramolecules are from 336 (polymer 7e) to 433° C. (polymer 7h) under nitrogen atmosphere where 95% of their mass is retained. In air, the decomposition temperatures are slightly lowered, and there are 15-25% residues left after being heated to 800° C. No clear phase transition is observed in DSC scans up to 300° C. This evidence reveals that the glass transition temperatures of the supramolecules are extremely high.

TABLE 2

Photophysical properties of polymers 7a to 7i in DMAC and as thin-films and model compounds 5a and 5b in DMAC

| Polymer (Measuring medium) | $\lambda_{max\,abs}$/nm ($\alpha_{max}/10^3 \times$ g$^{-1}$dm$^3$cm$^{-1}$) | $\lambda_{max,\,PL}$ (nm) | Color of emission | $\Phi_{PL}$ (%) |
|---|---|---|---|---|
| 5a (DMAC)$^a$ | 287 (25.3)$^f$ 326 (9.8)$^f$ 342 (6.0)$^f$ | 385 | Violet | 0.08 |
| 5b (DMAC)$^a$ | 288 (44.6)$^f$ 327 (26.4)$^f$ 344 (20.0)$^f$ | 447 | Blue | 0.62 |
| 7a (DMAC)$^b$ | 287 (71.2) 328 (39.2) 342 (20.2) | 450 | Blue | 0.45 |
| 7a (spin-coated film)$^c$ | / | 450 | Blue | / |
| 7a (casting film)$^d$ | / | 448 | Blue | 0.20 |
| 7b (DMAC)$^b$ | 290 (71.2) 320 (39.2) 343 (20.2) | 439 | Blue | 0.25 |
| 7b (spin-coated film)$^c$ | / | 440 | Blue | / |
| 7b (casting film)$^d$ | / | 436(sh)$^e$, 489 | Bluish green | 0.29 |
| 7c (DMAC)$^b$ | 287 (63.6) 328 (38.2) 345 (28.3) | 457 | Blue | 0.50 |
| 7c (spin-coated film)$^c$ | / | 465 | Blue | / |
| 7c (casting film)$^d$ | / | 465 | Blue | 0.42 |
| 7d (DMAC)$^b$ | 288 (50.6) 326 (28.6) 344 (21.5) | 441 | Blue | 0.44 |
| 7d (spin-coated film)$^c$ | / | 430 | Blue | / |
| 7d (casting film)$^d$ | / | 431 | Blue | 0.24 |
| 7e (DMAC)$^b$ | 287 (49.3) 328 (29.7) 342 (25.1) | 422 | Violet | 0.25 |
| 7e (spin-coated film)$^c$ | / | 488 | Green | / |
| 7e (casting film)$^d$ | / | 491 | Green | 0.15 |
| 7f (DMAC)$^b$ | 289 (74.7) | 457 | Blue | 0.77 |

TABLE 2-continued

Photophysical properties of polymers 7a to 7i in DMAC and as thin-films and model compounds 5a and 5b in DMAC

| Polymer (Measuring medium) | $\lambda_{max\,abs}$/nm ($\alpha_{max}$/10$^3$ × g$^{-1}$dm$^3$cm$^{-1}$) | $\lambda_{max,PL}$ (nm) | Color of emission | $\Phi_{PL}$ (%) |
|---|---|---|---|---|
| | 328 (46.5) | | | |
| | 346 (41.5) | | | |
| | 373 (24.8) | | | |
| 7f (spin-coated film)[c] | / | 546 | Green | / |
| 7f (casting film)[d] | / | 543 | Green | 0.48 |
| 7g (DMAC)[b] | 288 (115.8) | 456 | Blue | 0.34 |
| | 346 (55.6) | | | |
| | 372 (37.6) | | | |
| 7g (spin-coated film)[c] | / | 530 | Green | / |
| 7g (casting film)[d] | / | 517 | Green | 0.18 |
| 7h (DMAC)[b] | 287 (62.6) | 434, 518 (sh)[e] | White | 0.32 |
| | 328 (27.9) | | | |
| | 342 (23.5) | | | |
| 7h (spin-coated film)[c] | / | 535 | Green | / |
| 7h (casting film)[d] | / | 535 | Green | 0.55 |
| 7i (DMAC)[b] | 286 (36.3) | 440, 461, 556(sh)[e] | Greenish yellow | 0.49 |
| | 327 (27.7) | | | |
| | 391 (54.5) | | | |
| | 413 (47.3) | | | |
| 7i (spin-coated film)[c] | / | 567 | Yellow | / |
| 7i (casting film)[d] | / | 563 | Yellow | 0.42 |

[a]Concentration at 1 × 10$^{-5}$ mol dm$^{-3}$ in DMAC (N,N-dimethylacetamide)
[b]Concentration at 1 × 10$^{-5}$ g dm$^{-3}$ m DMAC (N,N-dimethylacetamide)
[c]The thickness of film was ~38-70 nm
[d]The thickness of film was ~0.5-2 μm
[e]Peak appears as shoulder
[f]Extinction coefficient ($\epsilon_{max}$) is expressed in unit of 10$^3$ × mol$^{-1}$ dm$^3$cm$^{-1}$ The absorption and photoluminescence properties of the polymers 7a to 7i are listed in table 2. The estimated bandgaps of the supramolecules are shown in Table 3. All the supramolecules and model compounds exhibit similar absorption features with $\lambda_{max}$ at 286-290 and 320-346 nm. Strong photoluminescence (PL) emissions spanning violet, blue, green, and yellow are obtained through variation of the supramolecular structure. The PL quantum yields ($\Phi$) of the supramolecules are from 25% for 7b and 7e to 77% for 7h in DMAC solution. The PL quantum efficiencies of the supramolecules as casting films are from 15% for 7e to 51% for 7h.

EXAMPLE 13

FIG. 7 shows representative UV-vis absorption spectrum of polymer 7a. In DMAC solution, a strong absorption band at $\lambda_{max}$ 287 nm ($\alpha_{max}$=73900 g$^{-1}$dm$^3$ cm$^{-1}$) and a shoulder at ca. $\lambda_{max}$ 328 to 342 nm ($\alpha_{max}$=36500 to 28800 g$^{-1}$dm$^3$ cm$^{-1}$) are observed. The optical band gap (absorption edge) is 3.19 eV. PL spectra of polymer 7a in solution and as thin-film are also demonstrated. Blue-color PL emissions are observed at $\lambda_{max}$ 450 and 448 nm both in DMAC and as casting film.

EXAMPLE 14

The PL emission spectra of the polymer 7c in solution and as thin-films are shown in FIG. 8. In DMAC, intense blue-color emission with a featureless emission band at $\lambda_{max}$ 457 nm is observed. The emission maximum of the polymer as spin-coated and casing films are shifted by 376 cm$^{-1}$ compared to that in solution respectively.

EXAMPLE 15

The PL spectra of the polymers 7a, 7f, 7g, and 7i as spin-coated films are represented in FIG. 9. By incorporating different linkages in the main chains or through side-group substitutions, the PL emission color of the supramolecules can be tuned. The emission colors of these polymers are blue (polymer 7a), green (polymer 7f), green (polymer 7g), and yellow (polymer 7i), which have PL emission peaks at $\lambda_{max}$ 450, 546, 530, and 567 nm, respectively.

EXAMPLE 16

The normalized PL spectra of the polymer 7h in DMAC, as spin-coated and casting films are shown in FIG. 10. White-light emission has been observed from the polymer 7h in DMAC with an emission maximum at 434 nm and a shoulder around 518 nm. In contrast, structureless yellow-light emission spectra of 7h as spin-coated and casting films with large stokes shift of 4350 cm$^{-1}$ are demonstrated respectively.

TABLE 3

HOMO-LUMO energy levels and bandgaps of supramolecules and model compounds

| Compound | LUMO (eV)[a] | HOMO (eV)[b] | Bandgap by absorption spectrum (eV)[c] |
|---|---|---|---|
| 5a | −3.18 | −6.64 | 3.46 |
| 5b | −3.38 | −6.64 | 3.26 |
| 7a | −3.29 | −6.48 | 3.19 |
| 7b | −3.37 | −6.63 | 3.26 |
| 7c | −3.43 | −6.63 | 3.20 |
| 7d | −3.37 | −6.63 | 3.26 |
| 7e | / | / | / |
| 7f | −3.61 | −6.56 | 2.95 |
| 7g | −3.67 | −6.59 | 2.92 |
| 7h | −3.63 | −6.55 | 2.92 |
| 7i | −3.94 | −6.58 | 2.64 |

[a]LUMO level was calculated from measured reduction potential versus ferrocene/ferrocenium couple in DMF solution. The absolute energy level of ferrocene is −4.8 eV
[b]The HOMO level was estimated from energy difference between LUMO energy level and bandgap
[c]The bandgap was estimated from absorption spectrum in DMAC by extrapolating the tail of the lowest energy peak.

EXAMPLE 17

The relative HOMO and LUMO levels of these supramolecules can be estimated by their reduction potentials and the optical band gaps. The electronic properties are summarized in table 3. FIG. 11 schematically illustrates the HOMO-LUMO levels and bandgaps of the supramolecules. The energy gaps between HOMO-LUMO levels of the supramolecules with oxymethylene linkage along their backbone are very similar, which are from 3.19 eV for 7a to 3.26 eV for 7d. These polymers show strong blue-light emissions in DMAC solution and as thin-films respectively. Polymers 7f, 7g and 7h exhibit similar electronic energy levels with LUMO energy levels from −3.61 to −3.67 eV and HOMO energy levels from −6.56 to −6.59 eV, and show strong green PL emissions as thin-films. Polymer 7h has the narrowest bandgap of 2.64 eV. A bright yellow-color emission of the polymer as thin-film is obtained.

An electroluminescent device according to this invention is schematically illustrated in FIG. 12. As an example of the present invention, the blue-light PLED with configuration of ITO/PEDOT/PSS/polymer 7a/Ca (30 Å)/Al (120 Å) was prepared. The device A was assembled as follows:

EXAMPLE 18

The device A was prepared on indium-tin-oxide (ITO) glass with sheet resistance of 20Ω/∀, which had been cleaned sequentially in detergent solution, deionized water, ethanol, and acetone. The wet-cleaning process was shown as following:

cleaning of the ITO glass with lint free tissues and acetone to remove adhering glass-particles ultrasonic cleaning in deionized water with glass-detergent for 10 minutes at 50° C.

rinsing with deionized water thoroughly ultrasonic cleaning in ethanol for 5 minutes at 50° C.

rinsing with deionized water thoroughly ultrasonic cleaning in acetone for 5 minutes at 40° C.

After wet-cleaning process, the ITO glass was dried at 130° C. for 24 h and treated in UV ozone cleaner for 10 mins to remove trace amount of organic substances. The poly(3,4-ethylenedioxythiophene)/(poly(styrenesulfonate) (PEDOT/PSS) and the polymer 7a were deposited on ITO by standard spin-coating manner. The layer-thickness of PEDOT/PSS was 30-100 nm. The layer-thickness of polymer 7a was 30-70 nm. The depositions of calcium (30 nm) and aluminum (120 nm) electrode were performed in high vacuum condition ($6 \times 10^{-6}$ Torr). The typical growth rate was 2 Å/s. The EL performance of the device was examined under air atmosphere without encapsulation.

EXAMPLE 19

The EL spectrum of polymer 7a at a bias voltage of 10 V showed an emission peak at 450 nm in FIG. 13. It was found to be similar to its corresponding PL emissions as spin-coated and casting films. The current density-voltage-luminance characteristics curves of the device A are also shown in FIG. 14. The blue-light EL intensity augmented with increasing bias voltage. The turn-on voltage was approximately 6 V. The maximum efficiency of the device was 0.8 cd/A. The maximum luminance of 1698 cd/m² was obtained at driving voltage of 13 V. The EL color of device A is blue (CIE coordinates: x=0.15, y=0.21).

EXAMPLE 20

This example illustrates the preparation of yellow-light PLED with configuration of ITO/PEDOT/PSS/polymer 7h/Ca(30 Å)/Al(120 Å). The device B was assembled similar to the device A.

The performance of the device B with polymer 7h is shown in FIG. 14. The current density-voltage-luminance characteristics curves of device B are presented in FIG. 15. The device exhibited an intense EL emission peak at 572 nm. The onset voltage of device B was approximately at 6 V. The efficiency and maximum luminance were 1.1 cd/A and 2382 cd/m² at 13 V respectively. The EL color of device B is yellow (CIE coordinates: x=0.46, y=0.50).

What is claimed is:

1. A supramolecule comprising at least two repeating structural units represented by the formula:

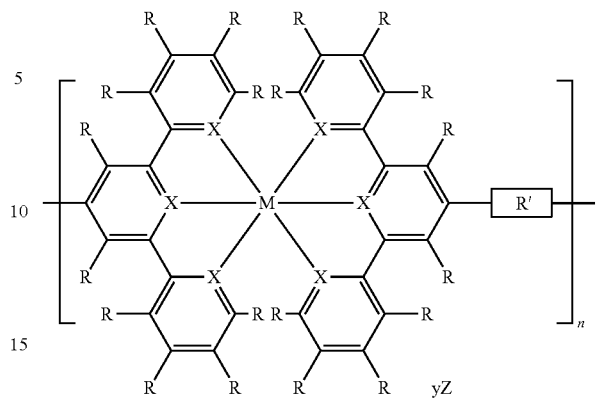

wherein M is zinc; R is independently in each occurrence and is hydrogen, halogen, alkyl, substituted alkyl, aryl, substituted aryl, or recognized donor or acceptor groups; X is independently in each occurrence and is a nitrogen or a carbon atom; R' is alkoxy, aryloxy, heteroaryloxy, alkyl, heteroaryl, alkyl ketone, aryl ketone, heteroaryl ketone, alkylester, arylester, arylamide, heteroarylester, heteroarylamide, alkylthio, arylthio, 2',5'-bis(alkyloxy)-1,1', 4',1"-terphenyl, 2,7-diphenyl-9,9-alkyl-9H-fluorene, phenylenevinylene, fluoroalkyl, fluoroaryl, amine, carboxylate, sulfonyl, alkyleneoxy, polyalkyleneoxy, or a combination thereof; n is an integer 2 to 100,000; Z is a counter ion and is acetate, acetylacetonate, cyclohexanebutyrate, ethylhexanoate, hexafluorophosphate, hexafluoroacetylacetonate, phosphate, sulfate, or tetrafluoroborate; and y is an integer of 0 to 4.

2. A supramolecule according to claim 1, wherein R is hydrogen.

3. A supramolecule according to claim 1, wherein X is nitrogen atom.

4. A supramolecule according to claim 1, wherein Z is hexafluorophosphate Ion ($PF_6^-$).

5. A supramolecule which is represented by formula:

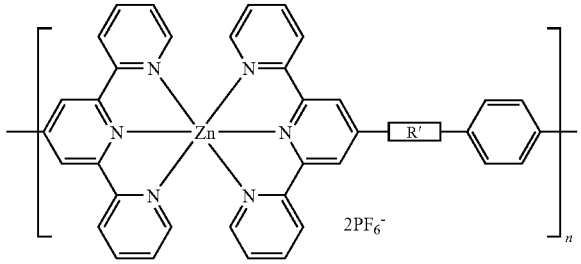

wherein n is an integer from 2 to 100,000 and R' is

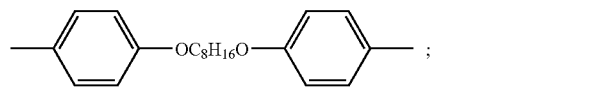;
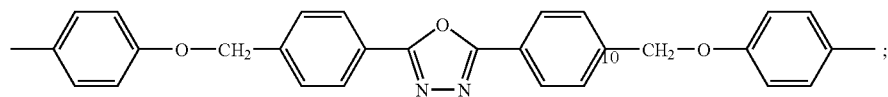;
;
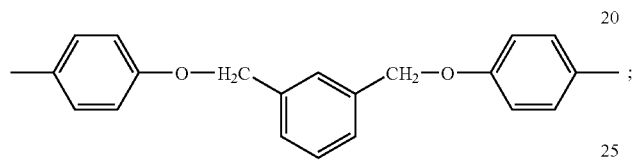;
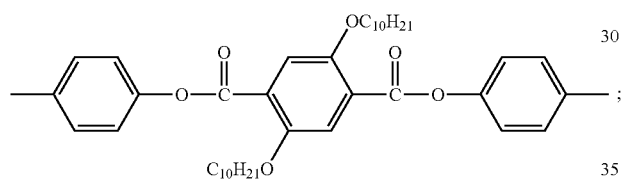;
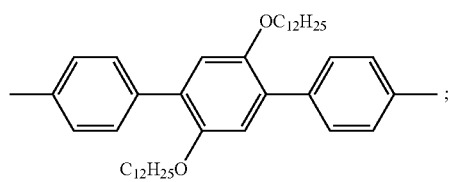;
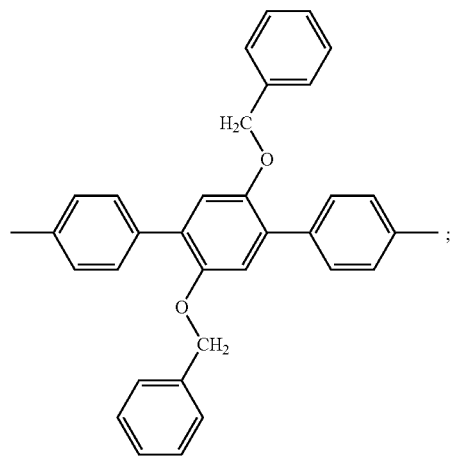;
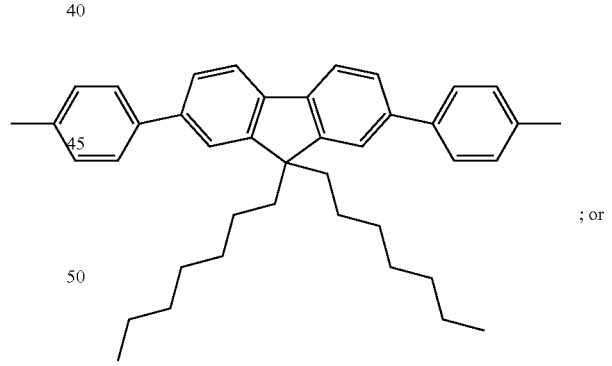; or
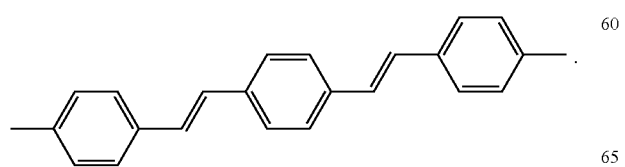.

6. A polymeric light-emitting diode (PLED) comprising:
(a) a transparent hole-injecting anode layer;
(b) a transparent hole-transporting layer;
(c) an active emissive layer comprising a supramolecule which includes at least one repeating structural unit having the following formula:

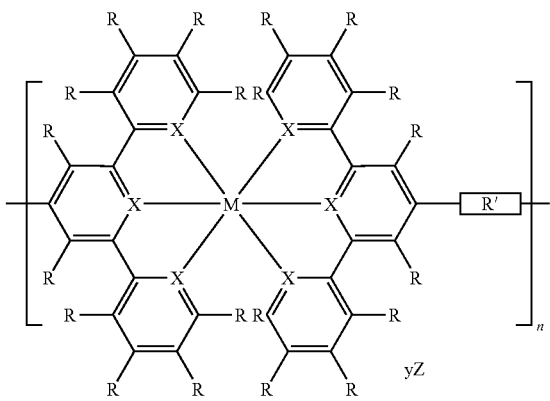

wherein M is zinc; R is independently in each occurrence and is selected from the group consisting of hydrogen, halogen, alkyl, substituted alkyl, aryl, substituted aryl, and recognized donor and acceptor groups; X is independently in each occurrence and is nitrogen or carbon atom; R' is selected from alkoxy, aryloxy, heteroaryloxy, alkyl, heteroaryl, alkyl ketone, aryl ketone, heteroaryl ketone, alkylester, arylester, heteroarylester, heteroarylamide, alkylthio, arylthio, 2',5'-bis(alkyloxy)-1,1', 4',1"-terphenyl, 2,7-diphenyl-9,9-alkyl-9H-fluorene, phenylenevinylene, fluoroalkyl, fluoroaryl, amine, carboxylate, sulfonyl, alkyleneoxy, polyalkyleneoxy, or combination thereof; n is an integer between 2 to 100,000; Z is a counter ion and is an acetate, acetylacetonate, cyclohexanebutyrate, ethylhexanoate, hexafluorophosphate, hexafluoroacetylacetonate, phosphate, sulfate, or tetrafluoroborate; and y is an integer of 0 to 4; and (d) an electron-injecting cathode layer.

7. A polymeric light-emitting diode according to claim 6, wherein the transparent hole-transporting layer is poly(aniline) (PANI) or poly(3,4 ethylenedioxythiophene)/(poly (styrenesulfonate) (PEDOT/PSS).

8. A polymeric light-emitting diode according to claim 6, wherein the transparent hole-injecting anode layer is a high work function metal or metal alloy.

9. A polymeric light-emitting diode according to claim 8, wherein the anode is gold, silver, copper, fluorine-tin-oxide (FTO), or indium-tin-oxide (ITO).

10. A polymeric light-emitting diode in according to claim 6, wherein the transparent electron-injecting cathode layer is a low work function metal or metal alloy.

11. A polymeric light-emitting diode according to claim 10, wherein the cathode is calcium, magnesium, lithium, sodium, aluminum, or silver.

12. A polymeric light-emitting diode according to claim 6, wherein M is zinc; R is hydrogen; X is nitrogen; and R' is

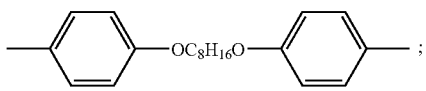

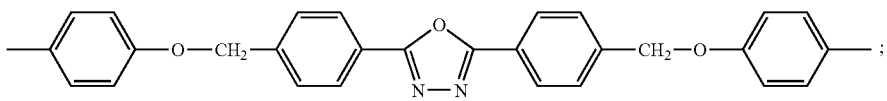

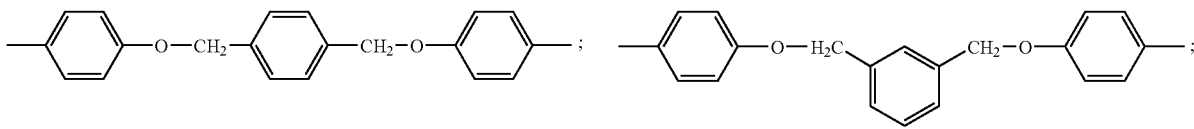

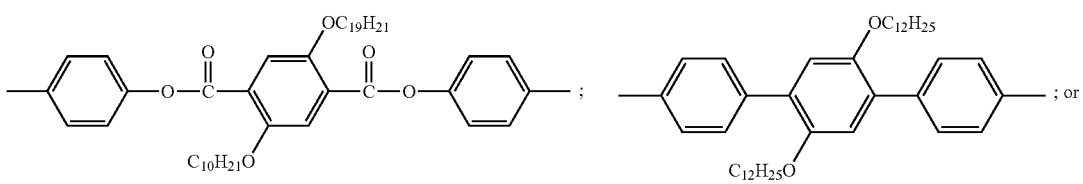

-continued
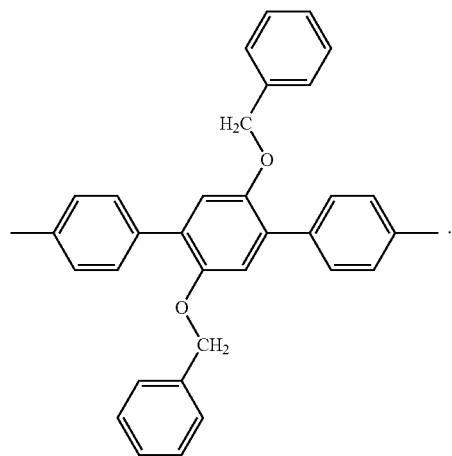
13. A polymeric light-emitting diode according to claim 12, wherein Z is hexafluorophosphate ion ($PF_6^-$).
14. A polymeric light-emitting diode according to claim 13, wherein M is Zn, y is 2, and R' is
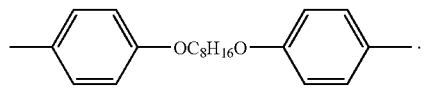
* * * * *